(12) United States Patent
Qi et al.

(10) Patent No.: US 11,098,123 B2
(45) Date of Patent: Aug. 24, 2021

(54) OCTS TECHNOLOGY-BASED PANCREATIC CANCER AND MALIGNANT MESOTHELIOMA CAR-T THERAPEUTIC VECTOR, CONSTRUCTION METHOD THEREFOR, AND USE THEREOF

(71) Applicant: SHANGHAI UNICAR-THERAPY BIO-MEDICINE TECHNOLOGY CO., LTD, Shanghai (CN)

(72) Inventors: Wei Qi, Shanghai (CN); Lei Yu, Shanghai (CN); Liqing Kang, Shanghai (CN); Gaowu Lin, Shanghai (CN); Zhou Yu, Shanghai (CN)

(73) Assignee: SHANGHAI UNICAR-THERAPY BIO-MEDICINE TECHNOLOGY CO., LTD, Shanghai (CN)

(*) Notice: Subject to any disclaimer, the term of this patent is extended or adjusted under 35 U.S.C. 154(b) by 0 days.

(21) Appl. No.: 16/617,529

(22) PCT Filed: Nov. 13, 2017

(86) PCT No.: PCT/CN2017/110673
§ 371 (c)(1),
(2) Date: Jan. 9, 2020

(87) PCT Pub. No.: WO2018/218879
PCT Pub. Date: Dec. 6, 2018

(65) Prior Publication Data
US 2020/0181269 A1 Jun. 11, 2020

(30) Foreign Application Priority Data
May 27, 2017 (CN) .......................... 201710390649.2

(51) Int. Cl.
*C07K 16/28* (2006.01)
*C07K 14/705* (2006.01)
*C12N 7/00* (2006.01)
*A61K 38/00* (2006.01)

(52) U.S. Cl.
CPC .... *C07K 16/2827* (2013.01); *C07K 14/70517* (2013.01); *C07K 16/2863* (2013.01); *C12N 7/00* (2013.01); *A61K 38/00* (2013.01); *C07K 2317/24* (2013.01); *C07K 2317/53* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2730/10144* (2013.01); *C12N 2740/15043* (2013.01); *C12N 2800/10* (2013.01)

(58) Field of Classification Search
CPC .......... C07K 16/2827; C07K 14/70517; C07K 16/2863; C07K 2317/24; C07K 2317/53; C07K 2317/622; C07K 2319/02; C07K 2319/03; C07K 2319/30; C07K 2319/33; C07K 2317/73; C07K 2317/31; C07K 16/30; C07K 14/70532; C07K 14/7051; C07K 14/70521; C07K 14/70578; C07K 2319/00; C12N 7/00; C12N 2730/10144; C12N 2740/15043; C12N 2800/10; C12N 5/0636; C12N 15/86; A61K 38/00; A61K 2039/852; A61K 2039/86; A61K 2039/5156; A61K 39/0011; A61K 35/17
See application file for complete search history.

(56) References Cited

U.S. PATENT DOCUMENTS

| 9,359,447 B2 * | 6/2016 | Feldman | C07K 14/7153 |
| 10,435,470 B2 * | 10/2019 | Zha | A61P 33/12 |
| 2019/0290693 A1 * | 9/2019 | Qi | A61P 35/00 |
| 2020/0181268 A1 * | 6/2020 | Qi | C07K 14/7051 |

FOREIGN PATENT DOCUMENTS

| CN | 105384825 A | 3/2016 |
| CN | 105602992 A | 5/2016 |
| CN | 105796597 A | 7/2016 |
| CN | 105969805 A | 9/2016 |
| CN | 106350533 A | 1/2017 |
| WO | 2016022630 A1 | 2/2016 |
| WO | 2016149578 A1 | 9/2016 |
| WO | 2017062952 A1 | 4/2017 |

OTHER PUBLICATIONS

Yelei Guo, et al., Chimeric Antigen Receptor-Modified T Cells for Solid Tumors: Challenges and Prospects, Journal of Immunology Research, Dec. 31, 2016, pp. 1-11, vol. 2016.
Burnet F. M., et al. Immunological Aspects of Malignant Disease. The Lancet, Jun. 3, 1967.

(Continued)

*Primary Examiner* — Phuong Huynh
(74) *Attorney, Agent, or Firm* — Bayramoglu Law Offices LLC

(57) ABSTRACT

An OCTS-based CAR-T vector for treating pancreatic cancer and malignant mesothelioma includes lentiviral skeleton plasmid, human EF1α promoter (SEQ ID NO: 14), OCTS chimeric receptor structural domain, and PDL1 single-chain antibody; the OCTS chimeric receptor structural domain consists of CD8 leader chimeric receptor signal peptide (SEQ ID NO: 15), PDL1 single-chain antibody light chain VL (SEQ ID NO: 16), PDL1 single-chain antibody heavy chain VH (SEQ ID NO: 17), mesothelin single-chain antibody light chain VL (SEQ ID NO: 18), mesothelin single-chain antibody heavy chain VH (SEQ ID NO: 19), antibody Inner-Linker (SEQ ID NO: 20), single-chain antibody Inter-Linker (SEQ ID NO: 21), CD8 Hinge chimeric receptor linker (SEQ ID NO: 22), CD8 Transmembrane chimeric receptor transmembrane domain (SEQ ID NO: 23), TCR chimeric receptor T cell activation domain (SEQ ID NO: 26) and chimeric receptor co-stimulator domain.

20 Claims, 9 Drawing Sheets
Specification includes a Sequence Listing.

(56) References Cited

OTHER PUBLICATIONS

Elanor J. Cheadle, et al., CAR T cells: driving the road from the colobrating to the clinic, Immunological Reviews, 2014, pp. 91-106, vol. 257.

Gregory L. Beatty, et al., Mesothelin-specific Chimeric Antigen Receptor mRNA-Engineered T cells Induce Anti-Tumor Activity in Solid Malignancies, Cancer Immunal Res., Feb. 1, 2014, pp. 112-120, 2(2).

Leonid Cherkassky, Human Car T cells with cell-intrinsic PD-1 checkpoint blockade resist tumor-mediated inhibition, The Journal of Clinical Investigation, Aug. 31, 2016, pp. 3130-3144, vol. 126, No. 8.

Hanlu Ding, et al., Delivering PD-1 inhibitory signal concomitant with blocking ICOS co-stimulation suppresses lups-like syndrome in autoimmune BXSB mice, Clinical Immunology, Jan. 4, 2006, pp. 258-267.

Haidong Dong, et al., Tumor-associated B7-H1 promotes T-cell apotosis: A potential mechanism of immune evasion, Nature Medicine, Aug. 2002, pp. 793-800, vol. 8, No. 8.

Intlekofer, A. M., et al. At the Bench: Preclinical Rationale for CTLA-4 and PD-1 Blockade as Cancer Immunotherapy, Journal of Leukocyte Biology, Jul. 2013, pp. 25-39, vol. 94.

Eloah Rabello Suarez, et al., Chimeric antigen receptor T cells secreting anti-PD-L1 antibodies more effectively regress renal cell carcinoma in a humanized mouse model, Oncotarget, Apr. 29, 2016, pp. 34341-34355, vol. 7, No. 23.

* cited by examiner

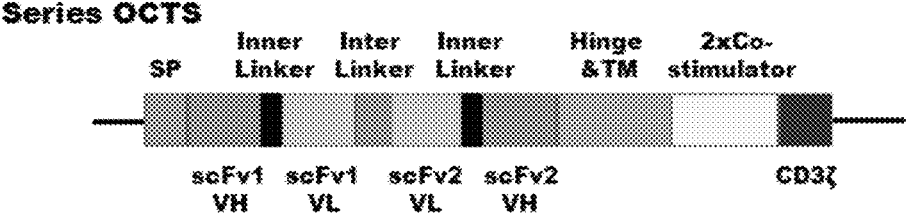
FIG. 4A
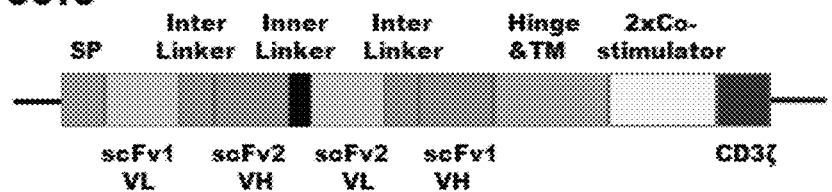
FIG. 4B
FIG. 4C

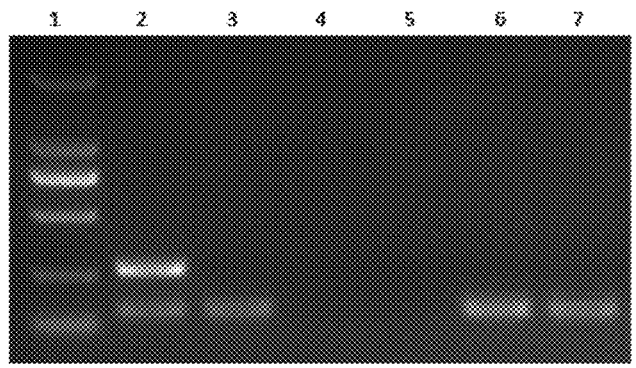

| PCR template | Products of PCR | Judgment and description |
|---|---|---|
| Positive control | There are a 280bp band and a 150bp band. | Established positiveness |
| | There is no or only one band. | Unestablished positiveness |
| Negative control | There is a 150bp band. | Established negativeness |
| | There is no or are more than 2 bands. | Unestablished negativeness |
| Sample | There are a 280bp band and a 150bp band. | Mycoplasma contamination |
| | There is only a 280bp band. | Severe mycoplasma contamination |
| | There is only a 150bp band. | No mycoplasma contamination |
| | There is no band. | Insufficient quantity of cells or inhabited PCR |

FIG. 8

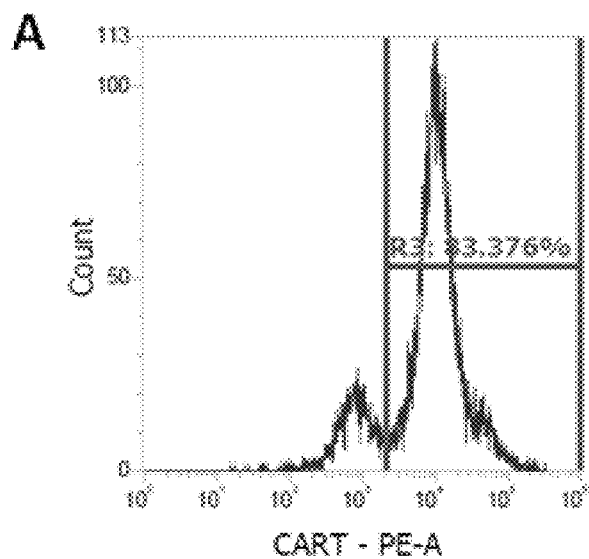

FIG. 9A

SEQUENCE LISTING

<160> NUMBER OF SEQ ID NOS: 39

<210> SEQ ID NO 1
<211> LENGTH: 861
<212> TYPE: DNA
<213> ORGANISM: Artificial sequence
<220> FEATURE:
<223> OTHER INFORMATION: the sequence is synthetized.

<400> SEQUENCE: 1

| | | | | | |
|---|---|---|---|---|---:|
| atgagtattc | aacatttccg | tgtcgccctt | attccctttt | ttgcggcatt | ttgccttcct | 60 |
| gttttttgctc | acccagaaac | gctggtgaaa | gtaaaagatg | ctgaagatca | gttgggtgca | 120 |
| cgagtgggtt | acatcgaact | ggatctcaac | agcggtaaga | tccttgagag | ttttcgcccc | 180 |
| gaagaacgtt | ttccaatgat | gagcactttt | aaagttctgc | tatgtggcgc | ggtattatcc | 240 |
| cgtattgacg | ccgggcaaga | gcaactcggt | cgccgcatac | actattctca | gaatgacttg | 300 |
| gttgagtact | caccagtcac | agaaaagcat | cttacggatg | gcatgacagt | aagagaatta | 360 |
| tgcagtgctg | ccataaccat | gagtgataac | actgcggcca | acttacttct | gacaacgatc | 420 |
| ggaggaccga | aggagctaac | cgcttttttg | cacaacatgg | gggatcatgt | aactcgcctt | 480 |
| gatcgttggg | aaccggagct | gaatgaagcc | ataccaaacg | acgagcgtga | caccacgatg | 540 |
| cctgtagcaa | tggcaacaac | gttgcgcaaa | ctattaactg | gcgaactact | tactctagct | 600 |
| tcccggcaac | aattaataga | ctggatggag | gcggataaag | ttgcaggacc | acttctgcgc | 660 |
| tcggcccttc | cggctggctg | gtttattgct | gataaatctg | gagccggtga | gcgtgggtct | 720 |
| cgcggtatca | ttgcagcact | ggggccagat | ggtaagccct | cccgtatcgt | agttatctac | 780 |
| acgacgggga | gtcaggcaac | tatggatgaa | cgaaatagac | agatcgctga | gataggtgcc | 840 |
| tcactgatta | agcattggta | a | | | | 861 |

<210> SEQ ID NO 2
<211> LENGTH: 674
<212> TYPE: DNA
<213> ORGANISM: Artificial sequence
<220> FEATURE:
<223> OTHER INFORMATION: the sequence is synthetized.

<400> SEQUENCE: 2

| | | | | | |
|---|---|---|---|---|---:|
| cccgtagaaa | agatcaaagg | atcttcttga | gatcctttt | ttctgcgcgt | aatctgctgc | 60 |
| ttgcaaacaa | aaaaaccacc | gctaccagcg | gtggtttgtt | tgccggatca | agagctacca | 120 |
| actctttttc | cgaaggtaac | tggcttcagc | agagcgcaga | taccaaatac | tgtccttcta | 180 |
| gtgtagccgt | agttaggcca | ccacttcaag | aactctgtag | caccgcctac | atacctcgct | 240 |
| ctgctaatcc | tgttaccagt | ggctgctgcc | agtggcgata | agtcgtgtct | taccgggttg | 300 |
| gactcaagac | gatagttacc | ggataaggcg | cagcggtcgg | gctgaacggg | gggttcgtgc | 360 |
| acacagccca | gcttggagcg | aacgacctac | accgaactga | gatacctaca | gcgtgagcta | 420 |
| tgagaaagcg | ccacgcttcc | cgaagggaga | aaggcggaca | ggtatccggt | aagcggcagg | 480 |
| gtcggaacag | gagagcgcac | gagggagctt | ccagggggaa | acgcctggta | tctttatagt | 540 |
| cctgtcgggt | ttcgccacct | ctgacttgag | cgtcgatttt | tgtgatgctc | gtcaggggggg | 600 |
| cggagcctat | ggaaaaacgc | cagcaacgcg | gcctttttac | ggttcctggc | cttttgctgg | 660 |
| ccttttgctc | acat | | | | | 674 |

<210> SEQ ID NO 3
<211> LENGTH: 147
<212> TYPE: DNA
<213> ORGANISM: Artificial sequence
<220> FEATURE:
<223> OTHER INFORMATION: the sequence is synthetized.

<400> SEQUENCE: 3

| | |
|---|---|
| atcccgcccc taactccgcc cagttccgcc cattctccgc cccatggctg actaattttt | 60 |
| tttatttatg cagaggccga ggccgcctcg gcctctgagc tattccagaa gtagtgagga | 120 |
| ggcttttttg gaggcctaga cttttgc | 147 |

<210> SEQ ID NO 4
<211> LENGTH: 228
<212> TYPE: DNA
<213> ORGANISM: Artificial sequence
<220> FEATURE:
<223> OTHER INFORMATION: the sequence is synthetized.

<400> SEQUENCE: 4

| | |
|---|---|
| gtagtcttat gcaatactct tgtagtcttg caacatggta acgatgagtt agcaacatgc | 60 |
| cttacaagga gagaaaaagc accgtgcatg ccgattggtg gaagtaaggt ggtacgatcg | 120 |
| tgccttatta ggaaggcaac agacgggtct gacatggatt ggacgaacca ctgaattgcc | 180 |
| gcattgcaga gatattgtat ttaagtgcct agctcgatac aataaacg | 228 |

<210> SEQ ID NO 5
<211> LENGTH: 180
<212> TYPE: DNA
<213> ORGANISM: Artificial sequence
<220> FEATURE:
<223> OTHER INFORMATION: the sequence is synthetized.

<400> SEQUENCE: 5

| | |
|---|---|
| ggtctctctg gttagaccag atctgagcct gggagctctc tggctaacta gggaacccac | 60 |
| tgcttaagcc tcaataaagc ttgccttgag tgcttcaagt agtgtgtgcc cgtctgttgt | 120 |
| gtgactctgg taactagaga tccctcagac cctttagtc agtgtggaaa atctctagca | 180 |

<210> SEQ ID NO 6
<211> LENGTH: 234
<212> TYPE: DNA
<213> ORGANISM: Artificial sequence
<220> FEATURE:
<223> OTHER INFORMATION: the sequence is synthetized.

<400> SEQUENCE: 6

| | |
|---|---|
| tgctagagat tttccacact gactaaaagg gtctgaggga tctctagtta ccagagtcac | 60 |
| acaacagacg ggcacacact acttgaagca ctcaaggcaa gctttattga ggcttaagca | 120 |
| gtgggttccc tagttagcca gagagctccc aggctcagat ctggtctaac cagagagacc | 180 |
| cagtacaagc aaaaagcaga tcttattttc gttgggagtg aattagccct tcca | 234 |

<210> SEQ ID NO 7
<211> LENGTH: 353
<212> TYPE: DNA
<213> ORGANISM: Artificial sequence
<220> FEATURE:
<223> OTHER INFORMATION: the sequence is synthetized.

<400> SEQUENCE: 7

| | |
|---|---|
| atgggtgcga gagcgtcagt attaagcggg ggagaattag atcgcgatgg gaaaaaattc | 60 |
| ggttaaggcc agggggaaag aaaaaatata aattaaaaca tatagtatgg gcaagcaggg | 120 |
| agctagaacg attcgcagtt aatcctggcc tgttagaaac atcagaaggc tgtagacaaa | 180 |
| tactgggaca gctacaacca tcccttcaga caggatcaga agaacttaga tcattatata | 240 |

```
atacagtagc aaccctctat tgtgtgcatc aaaggataga gataaaagac accaaggaag    300
ctttagacaa gatagaggaa gagcaaaaca aaagtaagac caccgcacag caa           353

<210> SEQ ID NO 8
<211> LENGTH: 233
<212> TYPE: DNA
<213> ORGANISM: Artificial sequence
<220> FEATURE:
<223> OTHER INFORMATION: the sequence is synthetized.

<400> SEQUENCE: 8
aggagctttg ttccttgggt tcttgggagc agcaggaagc actatgggcg cagcctcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcc           233

<210> SEQ ID NO 9
<211> LENGTH: 489
<212> TYPE: DNA
<213> ORGANISM: Artificial sequence
<220> FEATURE:
<223> OTHER INFORMATION: the sequence is synthetized.

<400> SEQUENCE: 9
tggggatttg ggttgctct ggaaaactca tttgcaccac tgctgtgcct tggaatgcta      60
gttggagtaa taaatctctg aacagattg gaatcacacg acctggatgg agtgggacag    120
agaaattaac aattacacaa gcttaataca ctccttaatt gaagaatcgc aaaaccagca    180
agaaaagaat gaacaagaat tattggaatt agataaatgg gcaagtttgt ggaattggtt    240
taacataaca aattggctgt ggtatataaa attattcata atgatagtag gaggcttggt    300
aggtttaaga atagttttg ctgtactttc tatagtgaat agagttaggc agggatattc    360
accattatcg tttcagaccc acctcccaac cccgagggga cccgacaggc ccgaaggaat    420
agaagaagaa ggtggagaga gagacagaga cagatccatt cgattagtga acggatctcg    480
acggttaac                                                            489

<210> SEQ ID NO 10
<211> LENGTH: 119
<212> TYPE: DNA
<213> ORGANISM: Artificial sequence
<220> FEATURE:
<223> OTHER INFORMATION: the sequence is synthetized.

<400> SEQUENCE: 10
ttttaaaaga aaagggggga ttggggggta cagtgcaggg gaaagaatag tagacataat     60
agcaacagac atacaaacta agaattaca aaaacaaatt acaaaaattc aaaattta       119

<210> SEQ ID NO 11
<211> LENGTH: 696
<212> TYPE: DNA
<213> ORGANISM: Artificial sequence
<220> FEATURE:
<223> OTHER INFORMATION: the sequence is synthetized.

<400> SEQUENCE: 11
atggcccagt ccaagcacgg cctgaccaag gagatgacca tgaagtaccg catggagggc     60
tgcgtggacg gccacaagtt cgtgatcacc ggcgagggca tcggctaccc cttcaagggc    120
aagcaggcca tcaacctgtg cgtggtggag ggcggccccct tgcccttcgc cgaggacatc    180
```

```
ttgtccgccg ccttcatgta cggcaaccgc gtgttcaccg agtaccccca ggacatcgtc      240
gactacttca agaactcctg ccccgccggc tacacctggg accgctcctt cctgttcgag      300
gacggcgccg tgtgcatctg caacgccgac atcaccgtga gcgtggagga gaactgcatg      360
taccacgagt ccaagttcta cggcgtgaac ttccccgccg acggcccccgt gatgaagaag     420 atgaccgaca actgggagcc ctcctgcgag aagatcatcc ccgtgcccaa gcagggcatc      480
ttgaagggcg acgtgagcat gtacctgctg ctgaaggacg gtggccgctt cgcctgccag      540
ttcgacaccg tgtacaaggc caagtccgtg ccccgcaaga tgcccgactg gcacttcatc      600
cagcacaagc tgacccgcga ggaccgcagc gacgccaaga accagaagtg gcacctgacc      660
gagcacgcca tcgcctccgg ctccgccttg ccctga                                696
```

```
<210> SEQ ID NO 12
<211> LENGTH: 575
<212> TYPE: DNA
<213> ORGANISM: Artificial sequence
<220> FEATURE:
<223> OTHER INFORMATION: the sequence is synthetized.

<400> SEQUENCE: 12
gcccctctcc ctccccccccc cctaacgtta ctggccgaag ccgcttggaa taaggccggt      60
gtgcgtttgt ctatatgtta ttttccacca tattgccgtc ttttggcaat gtgagggccc      120
ggaaacctgg ccctgtcttc ttgacgagca ttcctagggg tctttcccct ctcgccaaag      180
gaatgcaagg tctgttgaat gtcgtgaagg aagcagttcc tctggaagct tcttgaagac      240
aaacaacgtc tgtagcgacc ctttgcaggc agcggaaccc cccacctggc gacaggtgcc      300
tctgcggcca aaagccacgt gtataagata cacctgcaaa ggcggcacaa ccccagtgcc      360
acgttgtgag ttggatagtt gtggaaagag tcaaatggct caccctcaagc gtattcaaca     420 aggggctgaa ggatgcccag aaggtaccccc attgtatggg atctgatctg gggcctcggt    480
gcacatgctt tacatgtgtt tagtcgaggt taaaaaacgt ctaggccccc cgaaccacgg      540
ggacgtggtt ttccttttgaa aaacacgatg ataat                                575
```

```
<210> SEQ ID NO 13
<211> LENGTH: 592
<212> TYPE: DNA
<213> ORGANISM: Artificial sequence
<220> FEATURE:
<223> OTHER INFORMATION: the sequence is synthetized.

<400> SEQUENCE: 13
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctcttta tgaggagttg     180
tggcccgttg tcaggcaacg tggcgtggtg tgcactgtgt ttgctgacgc aacccccact      240
ggttggggca ttgccaccac ctgtcagctc ctttccggga cttcgctttt ccccctccct     300
attgccacgg cggaactcat cgccgcctgc cttgcccgct gctggacagg gctcggctg      360 ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc tg              592
```

<210> SEQ ID NO 14
<211> LENGTH: 1178
<212> TYPE: DNA
<213> ORGANISM: Artificial sequence
<220> FEATURE:
<223> OTHER INFORMATION: the sequence is synthetized.

<400> SEQUENCE: 14

```
gctccggtgc cgtcagtgg gcagagcgca catcgcccac agtccccgag aagttggggg      60
gaggggtcgg caattgaacc ggtgcctaga aaggtggcg cggggtaaac tgggaaagtg     120
atgtcgtgta ctggctccgc cttttttccg agggtggggg agaaccgtat ataagtgcag    180
tagtcgccgt gaacgttctt tttcgcaacg ggtttgccgc cagaacacag gtaagtgccg    240
tgtgtggttc ccgcgggcct ggcctcttta cgggttatgg cccttgcgtg ccttgaatta    300
cttccacctg gctgcagtac gtgattcttg atcccgagct tcgggttgga agtgggtggg    360
agagttcgag gccttgcgct taaggagccc cttcgcctcg tgcttgagtt gaggcctggc    420
ctgggcgctg gggccgccgc gtgcgaatct ggtggcacct tcgcgcctgt ctcgctgctt    480
tcgataagtc tctagccatt taaaatttt gatgacctgc tgcgacgctt ttttttctggc    540
aagatagtct tgtaaatgcg ggccaagatc tgcacactgg tatttcggtt tttggggccg    600
cgggcggcga cggggcccgt gcgtcccagc gcacatgttc ggcgaggcgg ggcctgcgag    660
cgcggccacc gagaatcgga cggggtagt ctcaagctgg ccggcctgct ctggtgcctg    720
gcctcgcgcc gccgtgtatc gccccgccct gggcggcaag gctggcccgg tcggcaccag    780
ttgcgtgagc ggaaagatgg ccgcttcccg gccctgctgc agggagctca aaatggagga    840
cgcggcgctc gggagagcgg gcgggtgagt cacccacaca aaggaaaagg gcctttccgt    900
cctcagccgt cgcttcatgt gactccactg agtaccgggc gccgtccagg cacctcgatt    960
agttctcgag cttttggagt acgtcgtctt taggttgggg ggaggggttt tatgcgatgg   1020
agtttcccca cactgagtgg gtggagactg aagttaggcc agcttggcac ttgatgtaat   1080
tctccttgga atttgcccct tttgagtttg gatcttggtt cattctcaag cctcagacag   1140
tggttcaaag tttttttctt ccatttcagg tgtcgtga                          1178
```

<210> SEQ ID NO 15
<211> LENGTH: 63
<212> TYPE: DNA
<213> ORGANISM: Artificial sequence
<220> FEATURE:
<223> OTHER INFORMATION: the sequence is synthetized.

<400> SEQUENCE: 15

```
atggccttac cagtgaccgc cttgctcctg ccgctggcct tgctgctcca cgccgccagg      60
ccg                                                                  63
```

<210> SEQ ID NO 16
<211> LENGTH: 333
<212> TYPE: DNA
<213> ORGANISM: Artificial sequence
<220> FEATURE:
<223> OTHER INFORMATION: the sequence is synthetized.

<400> SEQUENCE: 16

```
gatattgtgc tgacccagag cccggcgagc ctggcggtga gcccgggcca gcgcgcgacc      60
attacctgcc gcgcgagcca gagcgtgagc accagcagca gcagctttat gcattggtat     120
cagcagaaac cgggccagcc gccgaaactg ctgattaaat atgcgagcaa cctggaaagc     180
```

```
ggcgtgccgg cgcgctttag cggcagcggc agcggcaccg attttaccct gaccattaac    240
ccggtggaag cgaacgatac cgcgaactat tattgccagc atagctggga aattccgtat    300
acctttggcc agggcaccaa actggaaatt aaa                                 333

<210> SEQ ID NO 17
<211> LENGTH: 348
<212> TYPE: DNA
<213> ORGANISM: Artificial sequence
<220> FEATURE:
<223> OTHER INFORMATION: the sequence is synthetized.

<400> SEQUENCE: 17
gaagtgcagc tggtggaaag cggcggcggc ctggtgaaac cgggcggcag cctgcgcctg     60
agctgcgcgg cgagcggctt tattttcgc agctatggca tgagctgggt cgcgccaggcg   120 ccgggcaaag gcctggaatg ggtggcgagc attagcagcg gcggcagcac ctattatccg    180
gatagcgtga aaggccgctt taccattagc cgcgataacg cgaaaaacag cctgtatctg    240
cagatgaaca gcctgcgcgc ggaagatacc gcggtgtatt attgcgcgcg cggctatgat    300
agcggctttg cgtattgggg ccagggcacc ctggtgaccg tgagcagc                348

<210> SEQ ID NO 18
<211> LENGTH: 324
<212> TYPE: DNA
<213> ORGANISM: Artificial sequence
<220> FEATURE:
<223> OTHER INFORMATION: the sequence is synthetized.

<400> SEQUENCE: 18
gatattcaga tgacgcaaag cccgtctacc ctgagtgcct ccattggtga ccgtgttacg     60
atcacctgtc gcgcatccga aggcatctat cattggctgg cttggtacca gcaaaaaccg    120
ggtaaagcgc cgaaactgct gatctataaa gcaagttccc tggcatcggg tgctccgagc    180
cgcttttcag gttcgggtag cggcaccgat ttcacgctga ccatctcatc gctgcagccg    240
gacgatttcg ctacctacta ctgccaacaa tactcaaact acccgctgac cttcggtgga    300
gggaccaagc tggagatcaa acgt                                           324

<210> SEQ ID NO 19
<211> LENGTH: 357
<212> TYPE: DNA
<213> ORGANISM: Artificial sequence
<220> FEATURE:
<223> OTHER INFORMATION: the sequence is synthetized.

<400> SEQUENCE: 19
caagtccaac tggtccaaag tggtgctgaa gtcaaacgcc cgggtgcctc cgtccaagtc     60
tcctgccgtg cctctggcta ctcgattaac acctattaca tgcagtgggt ccgtcaagca    120
ccgggtgcag gtctggaatg gatgggtgtc atcaatccgt ccggcgtgac ctcatatgcg    180
cagaaatttc aaggtcgcgt taccctgacg aacgatacca gcacgaatac cgtctacatg    240
cagctgaact ctctgacgag tgcagacacc gcggtgtatt actgcgcacg ttgggcactg    300
tggggcgatt tcggcatgga tgtttgggc aaaggtacgc tggtgaccgt tagctct       357

<210> SEQ ID NO 20
<211> LENGTH: 45
<212> TYPE: DNA
<213> ORGANISM: Artificial sequence
<220> FEATURE:
<223> OTHER INFORMATION: the sequence is synthetized.
```

```
<400> SEQUENCE: 20
ggtggcggtg gctcgggcgg tggtgggtcg ggtggcggcg gatct              45

<210> SEQ ID NO 21
<211> LENGTH: 57
<212> TYPE: DNA
<213> ORGANISM: Artificial sequence
<220> FEATURE:
<223> OTHER INFORMATION: the sequence is synthetized.

<400> SEQUENCE: 21
gcctccacca agggcccatc tgtcttcccc ctggcccca gctcctctgg ctccgga    57

<210> SEQ ID NO 22
<211> LENGTH: 141
<212> TYPE: DNA
<213> ORGANISM: Artificial sequence
<220> FEATURE:
<223> OTHER INFORMATION: the sequence is synthetized.

<400> SEQUENCE: 22
accacgacgc cagcgccgcg accaccaaca ccggcgccca ccatcgcgtc gcagcccctg   60
tccctgcgcc cagaggcgtg ccggccagcg gcggggggcg cagtgcacac gaggggggctg  120 gacttcgcct gtgatatcta c                                          141

<210> SEQ ID NO 23
<211> LENGTH: 66
<212> TYPE: DNA
<213> ORGANISM: Artificial sequence
<220> FEATURE:
<223> OTHER INFORMATION: the sequence is synthetized.

<400> SEQUENCE: 23
atctgggcgc ccttggccgg gacttgtggg gtccttctcc tgtcactggt tatcacccctt  60 tactgc                                                           66

<210> SEQ ID NO 24
<211> LENGTH: 123
<212> TYPE: DNA
<213> ORGANISM: Artificial sequence
<220> FEATURE:
<223> OTHER INFORMATION: the sequence is synthetized.

<400> SEQUENCE: 24
aggagtaaga ggagcaggct cctgcacagt gactacatga acatgactcc ccgccgcccc   60
gggcccaccc gcaagcatta ccagccctat gccccaccac gcgacttcgc agcctatcgc  120
tcc                                                              123

<210> SEQ ID NO 25
<211> LENGTH: 111
<212> TYPE: DNA
<213> ORGANISM: Artificial sequence
<220> FEATURE:
<223> OTHER INFORMATION: the sequence is synthetized.

<400> SEQUENCE: 25
cgccgcgatc agcgcctgcc gccggatgcg cataaaccgc cgggcggcgg cagctttcgc   60
accccgattc aggaagaaca ggcggatgcg catagcaccc tggcgaaaat t          111
```

```
<210> SEQ ID NO 26
<211> LENGTH: 336
<212> TYPE: DNA
<213> ORGANISM: Artificial sequence
<220> FEATURE:
<223> OTHER INFORMATION: the sequence is synthetized.

<400> SEQUENCE: 26
cgcgtgaaat ttagccgcag cgcggatgcg ccggcgtatc agcagggcca gaaccagctg      60
tataacgaac tgaacctggg ccgccgcgaa gaatatgatg tgctggataa acgccgcggc     120
cgcgatccgg aaatgggcgg caaaccgcgc cgcaaaaacc cgcaggaagg cctgtataac     180
gaactgcaga aagataaaat ggcggaagcg tatagcgaaa ttggcatgaa aggcgaacgc     240
cgccgcggca aaggccatga tggcctgtat cagggcctga gcaccgcgac caaagatacc     300
tatgatgcgc tgcatatgca ggcgctgccg ccgcgc                              336

<210> SEQ ID NO 27
<211> LENGTH: 1557
<212> TYPE: DNA
<213> ORGANISM: Artificial sequence
<220> FEATURE:
<223> OTHER INFORMATION: the sequence is synthetized.

<400> SEQUENCE: 27
atgaactcct tctccacaag cgccttcggt ccagttgcct tctccctggg gctgctcctg      60
gtgttgcctg ctgccttccc tgccccagat attgtgctga cccagagccc ggcgagcctg     120
gcggtgagcc cgggccagcg cgcgaccatt acctgccgcg cgagccagag cgtgagcacc     180
agcagcagca gctttatgca ttggtatcag cagaaaccgg gccagccgcc gaaactgctg     240
attaaatatg cgagcaacct ggaaagcggc gtgccggcgc gctttagcgg cagcggcagc     300
ggcaccgatt ttaccctgac cattaacccg gtggaagcga cgataccgc gaactattat      360 tgccagcata gctgggaaat tccgtatacc tttggccagg gcaccaaact ggaaattaaa     420
ggtggcggtg gctcgggcgg tggtgggtcg ggtggcggcg gatctgaagt gcagctggtg     480
gaaagcggcg gcggcctggt gaaaccgggc ggcagcctgc gcctgagctg cgcggcgagc     540
ggctttattt ttcgcagcta tgcatgagc tgggtgcgcc aggcgccggg caaaggcctg     600
gaatgggtgg cgagcattag cagcggcggc agcacctatt atccggatag cgtgaaaggc     660
cgctttacca ttagccgcga taacgcgaaa aacagcctgt atctgcagat gaacagcctg     720
cgcgcggaag ataccgcggt gtatgattgc gcgcgcggct atgatagcgg ctttgcgtat     780
tggggccagg gcaccctggt gaccgtgagc agcggtggcg gtggctcggg cggtggtggg     840
tcgggtggcg gcggatctga accgaaaagc tgcgacaaaa ctcacacatg cccaccgtgc     900
ccagcacctg aactcctggg gggaccgtca gtcttcctct tcccccccaaa acccaaggac     960 accctcatga tctcccggac ccctgaggtc acatgcgtgg tggtggacgt gagccacgaa    1020
gaccctgagg tcaagttcaa ctggtacgtg gacggcgtgg aggtgcataa tgccaagaca    1080
aagccgcggg aggagcagta caacagcacg taccgtgtgg tcagcgtcct caccgtcctg    1140
caccaggact ggctgaatgg caaggagtac aagtgcaagg tctccaacaa agccctccca    1200
gcccccatcg agaaaaccat ctccaaagcc aaagggcagc cccgagaacc acaggtgtac    1260
accctgcccc catcccggga ggagatgacc aagaaccagg tcagcctgac ctgcctggtc    1320
aaaggcttct atcccagcga catcgccgtg gagtgggaga gcaatgggca gccggagaac    1380
aactacaaga ccacgcctcc cgtgctggac tccgacggct ccttcttcct ctacagcaag    1440
```

```
ctcaccgtgg acaagagcag gtggcagcag gggaacgtct tctcatgctc cgtgatgcac    1500
gaggctctgc acaaccacta cacgcagaag agcctctccc tgtctccggg taaatga       1557
```

<210> SEQ ID NO 28
<211> LENGTH: 36
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 28

```
attcaaaatt ttatcgatgc tccggtgccc gtcagt                              36
```

<210> SEQ ID NO 29
<211> LENGTH: 22
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 29

```
tcacgacacc tgaaatggaa ga                                             22
```

<210> SEQ ID NO 30
<211> LENGTH: 46
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 30

```
catttcaggt gtcgtgagga tccgccacca tggcgctgcc ggtgac                   46
```

<210> SEQ ID NO 31
<211> LENGTH: 33
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 31

```
ggggagggag aggggcttag cgcggcggca gcg                                 33
```

<210> SEQ ID NO 32
<211> LENGTH: 17
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 32

```
gcccctctcc ctccccc                                                   17
```

```
<210> SEQ ID NO 33
<211> LENGTH: 25
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 33
attatcatcg tgtttttcaa aggaa                                    25

<210> SEQ ID NO 34
<211> LENGTH: 44
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 34
aaaacacgat gataatgcca ccatgaactc cttctccaca agcg               44

<210> SEQ ID NO 35
<211> LENGTH: 46
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 35
aatccagagg ttgattgtcg acgaattctc atttgcccgg gctcag             46

<210> SEQ ID NO 36
<211> LENGTH: 21
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 36
cctttccggg actttcgctt t                                        21

<210> SEQ ID NO 37
<211> LENGTH: 20
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 37
gcagaatcca ggtggcaaca                                          20

<210> SEQ ID NO 38
<211> LENGTH: 21
<212> TYPE: DNA
<213> ORGANISM: Artificial sequence
```

```
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 38
catgtacgtt gctatccagg c                                          21

<210> SEQ ID NO 39
<211> LENGTH: 21
<212> TYPE: DNA
<213> ORGANISM: Artificial sequence
<220> FEATURE:
<223> OTHER INFORMATION: the sequence is synthetized.
<220> FEATURE:
<221> NAME/KEY: misc_feature
<223> OTHER INFORMATION: Primer

<400> SEQUENCE: 39
ctccttaatg tcacgcacga t                                          21
```

OCTS TECHNOLOGY-BASED PANCREATIC CANCER AND MALIGNANT MESOTHELIOMA CAR-T THERAPEUTIC VECTOR, CONSTRUCTION METHOD THEREFOR, AND USE THEREOF

CROSS REFERENCE TO THE RELATED APPLICATIONS

This application is the national phase entry of International Application No. PCT/CN2017/110673, filed on Nov. 13, 2017, which is based upon and claims priority to Chinese Patent Application No. 201710390649.2, filed on May 27, 2017, the entire contents of which are incorporated herein by reference.

TECHNICAL FIELD

This invention belongs to the field medical biology, specifically relating to a vector, especially an OCTS-based CAR-T vector for treating pancreatic cancer and malignant mesothelioma. Also, this invention relates to the preparation method and application of the vector.

BACKGROUND

The theoretical basis of tumor immunotherapy is that the immune system can identify tumor-associated antigens and regulate the body to attack tumor cells (highly specific cytolysis). In the 1950s, Burnet and Thomas made the theory of "immunological surveillance" that holds that mutational tumor cells that often occur in the body can be identified and eliminated by the immune system, laying a theoretical foundation for tumor immunotherapy [Burnet F M. Immunological aspects of malignant disease. Lancet, 1967; 1: 1171-4]. Then, a host of tumor immunotherapies, including cytokine therapy, monoclonal antibody therapy, adoptive immunotherapy and vaccine therapy, have been applied to clinical practice.

In 2013, CAR-T, a more advanced tumor immunotherapy, was successfully put to clinical use, and showed unprecedented clinical effects. CAR-T, short for Chimeric Antigen Receptor T-Cell Immunotherapy, feeds the chimeric molecule composed of promoter, antigen recognition domain, co-stimulator, effector domain, etc. into T cell genome, with transgenic method, so as to enable T cells to integrate the recognition, signal transduction, killing and other functions of target cells to achieve specific killing of target cells [Eleanor J. Cheadle, et al. CAR T cells: driving the road from the laboratory to the clinic. Immunological Reviews 2014. Vol. 257: 91-106]. Clinically, the most leading CAR-T is Novartis' CLT019. For patients having refractory-relapsed acute lymphoblastic leukemia and treated with CLT019, the six-month tumor progression-free survival rate can reach 67%, and the longest response time can be more than two years. By cooperating with hospitals, Shanghai Unicar Biomedical Technology Co., Ltd., a Shanghai-based company, treated 36 patients with refractory-relapsed acute lymphoblastic leukemia by February 2017, among whom 24 as a percentage of 66.6% experienced complete remission. It is a subversive breakthrough in anti-cancer research. CAR-T may be one of the therapies that are the most likely to cure cancer, and was named the best in top 10 breakthroughs of science and technology 2013 by the journal Science.

In spite of current significant effect of CAR-T in treating B lymphocytic leukemia and several other kinds of hematologic malignancies, there are still some limitations of the therapy. At present, a chimeric antigen receptor (CAR) can only recognize a kind of antigen target, while tumor cells are a complex colony, and once tumor cells containing corresponding antigens are eliminated, there will be rapid proliferation of tumor cells containing no corresponding antigens, thereby giving rise to tumor recurrence after some time. Hence, to enable CAR-T to simultaneously recognize two kinds of antigens, there are two alternative schemes: one is to transduce two groups of CARs into primary T lymphocytes once by building them into a lentiviral transgenic vector; the other is to separately transduce two groups of CARs into primary T lymphocytes by transducing two lentiviral transgenic vectors twice.

The disadvantage of the first scheme is that precious volume of lentiviral transgenic vector is occupied, which is not good for loading other functional components; efficiency in package of transgenic vector is low; efficiency in gene transduction is very low, making the transduction into primary T lymphocytes very difficult.

The disadvantage of the second scheme is that it needs two transductions with relatively low comprehensive efficiency and long time of transduction, and primary cells are easy to age, thus resulting in decline in proliferation ability and killing function and affecting the efficacy of tumor clearance.

Mesothelin is a tumor-associated antigen expressed in most malignant pleural mesothelioma, pancreatic cancer, ovarian cancer and some lung cancers and in normal tissues in a narrow range and low quantity, and thus can be used as the immunotherapeutic target for malignant pleural mesothelioma, pancreatic cancer, ovarian cancer (Gregory L. Beatty, Carl H. June et al. Mesothelin-Specific Chimeric Antigen Receptor mRNA-Engineered T Cells Induce Antitumor Activity in Solid Malignancies. Cancer Immunol Res 2014:2:112-120).

There is the overexpression of PDL1 in most cancerous tissues, including NSCLC (Non-Small Cell Lung Cancer), melanoma, breast cancer, glioma, lymphoma, leukemia, as well as various urinary tumors, digestive tract tumors and reproductive system tumors [Intlekofer A M, Thompson C B. At the bench: preclinical rationale for CTLA-4 and PD-1 blockade as cancer immunotherapy[J]. J Leukoc Biol, 2013, 94(1):25-39.]. In mouse and human tumor cells, Parsa discovered IFN-γ abnormally secreted by T cells, and IFN-γ can induce the high expression of PDL1 on tumor cells [Ding H, Wu X, Wu J, et al. Delivering PD-1 inhibitory signal concomitant with blocking ICOS co-stimulation suppresses lupus-like syndrome in autoimmune BXSB mice[J]. Clin Immunol, 2006, 118(2/3):258-267.]. High expression of PDL1 can inhibit the signals of RAS and PI3K/AKT to control the expression of cell cycle checkpoint protein and proteins related to cell proliferation to finally cause the proliferation of T cells to be suppressed. Through the in-vitro experiments by and mouse models of Dong, et al, it is also discovered that activation of PD-1/PDL1 signals can induce the apoptosis of specific CTL, decreasing sensitivity to the cytotoxic effect of CTL and causing the immune evasion of tumor cells [Dong H, Strome S E, Salomao D R, et al. Tumor-associated B7-H1 promotes T-cell apoptosis: a potential mechanism of immune evasion [J]. Nat Med, 2002, 8(8):793-800.].

So far, there has been no report on CAR-T overcoming the aforesaid disadvantages and against the antigens mesothelin and PDL1.

SUMMARY

One of the technical problems to be solved by the invention is to provide an OCTS-based CAR-T vector for treating pancreatic cancer and malignant mesothelioma. First of all, it only needs one transduction with high efficiency in transduction and without prejudice to the curative effect of CAR-T; second, it doesn't occupy the precious volume of lentiviral transgenic vector, which is good for loading other functional components; third, it can efficiently close PDL1, block negative control signals and be clinically used to suppress tumor immune evasion, thus improving the curative effect of CAR-T in cellular immunotherapy.

The second technical problem to be solved by the invention is to provide a preparation method of the vector.

The third technical problem to be solved by the invention is to provide the application of the vector.

To solve such technical problems, the invention adopts the following technical scheme:

In the first aspect, the invention provides an OCTS-based CAR-T vector for treating pancreatic cancer and malignant mesothelioma, consisting of lentiviral skeleton plasmid, human EF1α promoter, OCTS chimeric receptor structural domain, and PDL1 single-chain antibody;

The said lentiviral skeleton plasmid consists of AmpR sequence containing ampicillin resistance gene and for vast expansion of target bacterial strain, as shown in SEQ ID NO: 1;

Prokaryotic replicon pUC Ori sequence for plasmid replication, as shown in SEQ ID NO: 2;

Viral replicator SV40 Ori sequence for enhancing replication in eukaryotic cells, as shown in SEQ ID NO: 3; lentiviral packaging cis-element for lentiviral packaging; ZsGreen1 green fluorescent protein, as shown in SEQ ID NO: 11; IRES ribosome binding sequence, as shown in SEQ ID NO: 12; eWPRE enhanced marmot hepatitis B virus post-transcriptional controlling element for enhancing transgenic expression efficiency, as shown in SEQ ID NO: 13;

The sequence of the said human EF1α promoter is shown in SEQ ID NO: 14;

The said OCTS chimeric receptor structural domain consists of CD8 leader chimeric receptor signal peptide, as shown in SEQ ID NO: 15, PDL1 single-chain antibody light chain VL, as show in SEQ ID NO: 16, PDL1 single-chain antibody heavy chain VH, as show in SEQ ID NO: 17, mesothelin single-chain antibody light chain VL, as show in SEQ ID NO: 18, mesothelin single-chain antibody heavy chain VH, as show in SEQ ID NO: 19, antibody Inner-Linker, as shown in SEQ ID NO: 20, single-chain antibody Inter-Linker, as shown in SEQ ID NO: 21, CD8 Hinge chimeric receptor linker, as shown in SEQ ID NO: 22, CD8 Transmembrane chimeric receptor transmembrane domain, as shown in SEQ ID NO: 23, TCR chimeric receptor T cell activation domain and chimeric receptor co-stimulator domain, as shown in SEQ ID NO: 26; the said chimeric receptor co-stimulator domains are selected from any one or more combinations of 4-1BB, ICOS, CD27, OX40, CD28, MYD88, IL1R1, CD70, TNFRSF19L, TNFRSF27, TNFRSF1OD, TNFRSF13B, TNFRSF18, CD134 and other tumor necrosis factor receptor superfamilies (TNFRSF).

The said lentiviral packaging cis-element can employ either the second-generation lentiviral vector or the third-generation lentiviral vector. The second-generation lentiviral vectors employed by the said lentiviral packaging cis-element include lentiviral 5 terminal LTR, as shown in SEQ ID NO: 5, lentiviral 3 terminal Self-Inactivating LTR, as shown in SEQ ID NO: 6, Gag cis-element, as shown in SEQ ID NO: 7, RRE cis-element, as shown in SEQ ID NO: 8, env cis-element, as shown in SEQ ID NO: 9, cPPT cis-element as shown in SEQ ID NO: 10. The third-generation lentiviral vectors employed by the said lentiviral packaging cis-element include lentiviral 5 terminal LTR, as shown in SEQ ID NO: 5, lentiviral 3 terminal self-Inactivating LTR, as shown in SEQ ID NO: 6, Gag cis-element, as shown in SEQ ID NO: 7, RRE cis-element, as shown in SEQ ID NO: 8, env cis-element, as shown in SEQ ID NO: 9, cPPT cis-element, as shown in SEQ ID NO: 10, and RSV promoter as shown, in SEQ ID NO: 4. The invention preferably employs the third-generation lentiviral vectors.

Preferably, the said PDL1 single-chain antibody light chain VL, as show in SEQ ID NO: 16, PDL1 single-chain antibody heavy chain VH, as show in SEQ ID NO: 17, mesothelin single-chain antibody light chain VL, as show in SEQ ID NO: 18, mesothelin single-chain antibody heavy chain VH, as show in SEQ ID NO: 19, antibody Inner-Linker, as shown in SEQ ID NO: 20, single-chain antibody Inter-Linker, as shown in SEQ ID NO: 21, are connected in serial or turned way; specifically, the said serial connection is that PDL1 single-chain antibody light chain VL is connected with mesothelin single-chain antibody light chain VL through single-chain antibody Inter-Linker and with PDL1 single-chain antibody heavy chain VH through antibody Inner-Linker, while mesothelin single-chain antibody light chain VL is connected with mesothelin single-chain antibody heavy chain VH through antibody Inner-Linker, i.e., pOCTS-PMs (see FIGS. 4A and 4C); specifically, the said turned connection is that mesothelin single-chain antibody light chain VL is connected with mesothelin single-chain antibody heavy chain VH through antibody Inner-Linker, while PDL1 single-chain antibody light chain VL is connected with mesothelin single-chain antibody heavy chain VH through single-chain antibody Inter-Linker, and PDL1 single-chain antibody heavy chain VH is connected with mesothelin single-chain antibody light chain VL through antibody Inter-Linker, i.e., pOCTS-PMt (see FIGS. 4B and 4C).

Preferably, the sequence of the said PDL1 single-chain antibody is shown in SEQ ID NO: 27.

Preferably, there are 6 enhanced nucleotide mutations of the said eWPRE enhanced marmot hepatitis B virus post-transcriptional controlling element: g.396G>A, g.397C>T, g.398T>C, g.399G>A, g.400A>T, g.411A>T.

Preferably, the whole OCTS structural gene expression is started by the said human EF1α promoter, and the said CD8 leader chimeric receptor signal peptide on the N terminal of OCTS coding sequence is used to guide the location of OCTS protein on cytomembrane; the said two groups of single-chain antibodies PDL1 single-chain antibody light chain VL, PDL1 single-chain antibody heavy chain VH, mesothelin single-chain antibody light chain VL and mesothelin single-chain antibody heavy chain VH are combined into double antigen recognition domain and used to recognize corresponding target antigens; the said CD8 Hinge chimeric receptor linker is used to anchor scFv on the outside of cytomembrane; the said CD8 Transmembrane chimeric receptor transmembrane domain is used to fix entire chimeric receptors on cytomembrane; the said CD28 chimeric receptor co-stimulator is used to stimulate in-vitro T lymphocyte activation and killing effect on in-vivo tumor cells; the said CD134 chimeric receptor co-stimulator is used to facilitate T lymphocyte proliferation and factor secretion and enhance tumor immunity, which is good for the long-term survival of memory T cells; the said TCR chimeric receptor T cell activation domain is used to activate the expression of downstream signals; the said PDL1 single-chain antibody can efficiently close PDL1, block negative control signals and be clinically used to suppress tumor immune evasion, thus improving the curative effect of CAR-T in cellular immunotherapy; when antigen recognition domain is bound to target antigens, signals will be transmitted into cells through chimeric receptors, thereby creating a series of biological effects such as T cell proliferation, increased cell factor secretion, increased antiapoptosis secretion, delayed cell death and target cell lysis.

Preferably, the said chimeric receptor co-stimulator domain employs the combination of CD28 chimeric receptor co-stimulator as shown in SEQ ID NO: 24 and CD134 chimeric receptor co-stimulator as shown in SEQ ID NO: 25.

Preferably, all the said PDL1 single-chain antibody light chain VL, PDL1 single-chain antibody heavy chain VH, mesothelin single-chain antibody light chain VL, mesothelin single-chain antibody heavy chain VH and PDL1 single-chain antibody have been humanized.

In the second aspect, the invention provides a preparation method of the said OCTS-based CAR-T vector for treating pancreatic cancer and malignant mesothelioma, including the following steps:

(1) Store on lentiviral skeleton plasmid the AmpR sequence containing ampicillin resistance gene as shown in SEQ ID NO: 1, prokaryotic replicon pUC On sequence as shown in SEQ ID NO: 2, virus replicon SV40 Ori sequence as shown in SEQ ID NO: 3, lentiviral packaging cis-element for lentiviral packaging, ZsGreen1 green fluorescent protein as shown in SEQ ID NO: 11, IRES ribosome binding sequence as shown in SEQ ID NO: 12, and eWPRE enhanced post-transcriptional regulatory element of Groundhog hepatitis B virus as shown in SEQ ID NO: 13;

(2) Combine into a design scheme for OCTS chimeric receptor the human EF1α promoter as shown in SEQ ID NO: 14, the said OCTS chimeric receptor structural domain and PDL1 single-chain antibody as shown in SEQ ID NO: 27, and clone the scheme into lentiviral skeleton plasmids by digestion, ligation and recombination to obtain pOCTS-PMs and pOCTS-PMt, recombinant lentiviral plasmids designed by the third-generation OCTS;

(3) Transfect HEK293T/17 cells by obtained recombinant lentiviral plasmids pOCTS-PMs and pOCTS-PMt with lentiviral packaging plasmids pPac-GP and pPac-R and membrane protein pEnv-G respectively. After gene transcription and expression in HEK293T/17 cells, recombinant lentiviral vector packaged successfully will be released into cell culture supernatants, and then collect supernatants containing recombinant lentiviral vectors;

(4) Purify obtained recombinant lentiviral supernatants with the method of column purification of filtration, adsorption and elution, and obtain recombinant lentiviral vectors lvOCTS-PMs and lvOCTS-PMt respectively.

Preferably, in step (4), the said filtration step is to control the volume of supernatant from 200 ml to 2000 ml, the vacuum degree from −0.5 MPA to 0.9 MPA to prevent the loss of vector caused by blockage. The said adsorption step is to control the PH value of solution from 6 to 8 to prevent the vector from inactivating due to the change of pH, and the said elution step is to control the ionic strength of eluent from 0.5 M to 1.0M to prevent the change of ionic strength leading to incomplete elution or inactivation of vector.

In the third aspect, the invention provides the application of the said vectors in the preparation of drugs for treating pancreatic cancer and malignant mesothelioma.

Compared with existing technologies, the invention has the following beneficial effects:

Based on current traditional CAR-T cellular therapy, by optimizing and modifying the structure of chimeric antigen receptor (CAR), the OCTS-CAR-T technology employed in the invention makes CARs able to recognize two antigens, thereby greatly expanding the recognition scope of CAR-T cells and making the elimination directed at tumor groups more thorough and with more lasting curative effect, avoids the batch culture of CAR-T cells, thereby greatly saving costs, avoids multiple reinfusion of different targeting CAR-T cells in patients, thus reducing the spending of patients and odds of recurrence and indirectly improving the life quality of patients, only needs one transduction with high efficiency in transduction and without prejudice to the curative effect of CAR-T, and does not occupy the precious volume of lentiviral transgenic vector, which is good for loading other functional components, and with high efficiency in transgenic vector package and gene transduction.

OCTS, short for One CAR with Two ScFvs, integrates two scFvs into a chimeric molecule (as shown in FIG. 1) by means of Series OCTS or Turn OCTS connection, to enable T lymphocyte HLA to independently recognize two tumor antigens and recognize more extensive targets compared with traditional CAR-T cells, thus further extending the scope of elimination of tumor cells. Basic design of OCTS involves two tumor-associated antigen (TAA) binding domains (which generally is scFv sector coming from monoclonal antibody and antigen binding domain), one extracellular linker domain, one transmembrane domain, two intracellular signal transduction domain and one effector domain. ScFv domain is a key factor determining the specificity and effectiveness of OCTS and the safety of gene modification of T cells. Upcoming clinical research stage of OCTS-CAR-T marks that CAR-T in cellular therapy is about to step into its 2.0 era.

The vector skeleton employed by the invention can be applied to both the second-generation and third-generation lentiviral vector structure. The major difference in structure between the second-generation and third-generation lentiviral vectors is shown in FIG. 2B. The invention give preference to the third-generation lentiviral vector (as shown in FIG. 2A), removes U3 region from 3'SIN LTR, thereby eliminating the possibility of self-replication of lentiviral vector and greatly improving the security, adds the cPPT and WPRE elements, thereby improving the transduction efficiency and transgenic expression efficiency, employs RSV promoter thereby ensuring the continuous and efficient transcription of core RNA in lentiviral vector packaging, and employs human EF1α promoter, thereby enabling CAR gene to be continuously expressed in human body for a long time.

In the invention, all the said PDL1 single-chain antibody light chain VL, PDL1 single-chain antibody heavy chain VH, mesothelin single-chain antibody light chain VL, mesothelin single-chain antibody heavy chain VH and PDL1 single-chain antibody have been humanized, and can effectively reduce the production of human anti-mouse antibodies (HAMA), extend the half life and effect of scFv and increase the lifetime of OCTS-CAR-T cells.

One or several combinations of co-stimulators used in the invention can enhance the proliferation rate, survival time, killing efficiency, immune memory and other specificities of transduced cells.

OCTS-CAR-T cells employed by the invention can be used for human clinical trials after being produced by GMP-level workshops.

Recombinant lentiviral vectors employed in the invention can realize the expression of double target chimeric antigen receptors of the combination of PDL1, mesothelin, etc. on human T lymphocytes, guide and activate the killing effect of T lymphocytes on PDL1, mesothelin and other positive cells, and be clinically used to treat pancreatic cancer, malignant mesothelioma and other mesothelin positive/PDL1 positive/both mesothelin and PDL1 positive malignant tumors.

The invention builds and forms recombinant lentiviral vectors through recombinant lentiviral vector skeleton, OCTS structural domain and PDL1 single-chain antibody, and recombinant lentiviral vectors obtained in such way can realize the expression of cellular programmed cell death 1 (PDL1) single-chain antibodies in human T lymphocytes, which can efficiently close PDL1, block negative control signals and be clinically used to suppress tumor immune evasion, thus improving the curative effect of CAR-T in cellular immunotherapy.

It can be seen that OCTS-CAR-T cells said in the invention will provide reliable guarantee for tumor cell therapy.

BRIEF DESCRIPTION OF THE DRAWINGS

FIGS. 2A-2B are schematic diagrams of the structure of the lentiviral vector said in the invention; wherein, FIG. 2A is a schematic diagram of the structure of the third-generation lentiviral vector employed by the invention, and FIG. 2B is a schematic diagram of the structure comparison of the second and third-generation lentiviral vectors;

FIGS. 4A-4C are schematic diagrams of the element order of OCTS structure in embodiment 1 of the invention; wherein, FIG. 4A is a schematic diagram of the structure of Series OCTS; FIG. 4B is a schematic diagram of the structure of Turn OCTS; FIG. 4C is a schematic diagram of the list of OCTS Symbols of OCTS structure;

FIGS. 5A-5D show enzyme digestion prediction and enzyme digestion agarose gel electrophoresis diagram of recombinant lentiviral plasmids pOCTS-PMs and pOCTS-PMt in embodiment 1 of the invention; wherein, FIG. 5A is a schematic diagram of the enzyme digestion prediction of pOCTS-PMs, and FIG. 5B is an enzyme digestion agarose gel electrophoresis diagram of pOCTS-PMs; FIG. 5C is a schematic diagram of the enzyme digestion prediction of pOCTS-PMt, and FIG. 5D is an enzyme digestion agarose gel electrophoresis diagram of pOCTS-PMt; in FIG. 5A, lane 1 is 1 kb DNA ladder Marker: the bands from top to bottom are 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; in FIG. 5A, lane 2 is the KpnI enzyme digestion prediction of pOCTS-PMs: the bands from top to bottom are 6254 bp, 4638 bp, 1525 bp; in FIG. 5B, lane 1 is the electrophoretic results of 1 kb DNA ladder Marker; in FIG. 5B, lane 2 is the KpnI enzyme digestion electrophoretic results of pOCTS-PMs; in FIG. 5C, lane 1 is 1 kb DNA ladder Marker: the bands from top to bottom are 10 kb, 8 kb, 6 kb, 5 kb, 4 kb, 3.5 kb, 3 kb, 2.5 kb, 2 kb, 1.5 kb, 1 kb, 750 bp, 500 bp, 250 bp; in FIG. 5C, lane 2 is ApaL I enzyme digestion prediction of pOCTS-PMt: the bands from top to bottom are 5032 bp, 4091 bp, 1731 bp, 1241 bp, 492 bp; in FIG. 5D, lane 1 is the electrophoretic results of 1 kb DNA ladder Marker; in FIG. 5D, lane 2 is the enzyme digestion electrophoretic results of pOCTS-PMt;

FIG. 8 is a schematic diagram of mycoplasma detection results of OCTS-CAR-T cells in embodiment 2 of the invention, where lane 1 is DL2000 marker, and the bands from top to bottom are 2 kb, 1 kb, 750 bp, 500 bp, 250 bp and 100 bp; lane 2 is a positive control; lane 3 is a negative control; lane 4 is PBS; lane 5 is lysate; lane 6 is OCTS-PMs-CAR-T cell; lane 7 is OCTS-PMt-CAR-T cell;

FIGS. 9A-9D are schematic diagrams of the results of flow cytometry of transduction efficiency and immunophenotyping of OCTS-CAR-T cell; wherein, FIG. 9A shows the results of transduction efficiency of OCTS-PMs-CAR-T cell; FIG. 9B shows the results of immunophenotyping of OCTS-PMs-CAR-T cell, FIG. 9C shows the results of transduction efficiency of OCTS-PMt-CAR-T cell; FIG. 9D shows the results of immunophenotyping of OCTS-PMt-CAR-T cell;

DETAILED DESCRIPTION OF THE EMBODIMENTS

Figure 1:
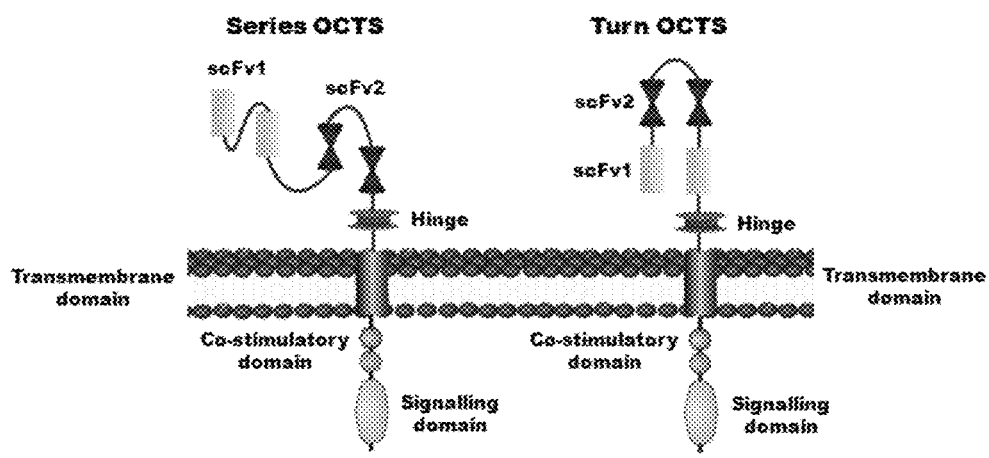
FIG. 1 is a schematic diagram of the OCTS chimeric receptor said in the invention, consisting of the schematic diagram of Series OCTS and Turn OCTS.
Figure 2A:
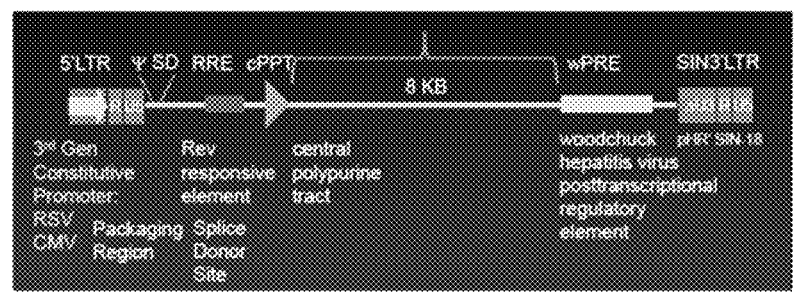
Figure 2B:
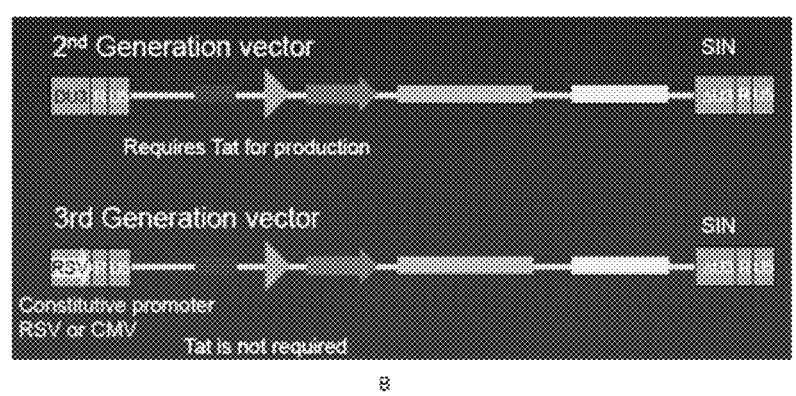

The invention is further described below in connection with specific implementation methods. It should be understood that the specific implementation methods described herein are expressed by way of examples and are not constrained by the invention. Without departing from the scope of the invention, the main features of the invention can be used in various implementation methods.

Materials

1. Lentiviral skeleton plasmid pLenti-3G basic, lentiviral packaging plasmids pPac-GP and pPac-R and membrane protein plasmid pEnv-G, HEK293T/17 cells, homologous recombinase, Oligo Annealing Buffer, MycoAlert Mycoplasma Detection Kit, endotoxin detection kit, $PDL1^+K562$, $^+K562$, $PDL1^+MESOTHELIN^+K562$ and K562 cells were bought from Shiao (Shanghai) Biomedical Technology Co., Ltd.; specific preparation method of lentiviral skeleton plasmid pLenti-3G basic has been disclosed in the patent application No. 201610008360.5 for an invention titled "A CAR-T Transgenic Vector Based on Replication-Competent Defective Recombinant Lentiviral vector as Well as Preparation Method and Application Thereof";

2. Fresh human peripheral blood provided by healthy donors;

3. Combination of OCTS-PMs and OCTS-PMt DNA sequences designed by Shanghai Unicar (see FIG. 4C), synthesized by Shanghai Generay Biotech Co., Ltd. and kept in the form of dry powder of oligonucleotides or plasmid;

4. Tool enzymes Kpn I, ApaL I, Cla I, EcoR I and T4 DNA ligase purchased from NEB;

5. 0.22 μm-0.8 μm PES filter purchased from Millipore;

6. D-PBS (−), 0.4% trypan blue, screen mesh, various cell-culture dishes, culture bags, and culture plates bought from Corning;
7. Opti-MEM, Pen-Srep, Hepes, FBS, AIM-V, RPMI 1640, DMEM, lipofectamine 3000 bought from Invitrogen;
8. Biotinylated protein L bought from GeneScript;
9. LDH detection kits bought from Promega;
10. Ficoll lymphocyte separation medium bought from GE;
11. 20% human albumin solution bought from CSL Behring;
12. CryoPremium freezing medium and sorting buffer solution bought from Shanghai Unicar;
13. rIL-2, rIL-7, rIL-15, rIL-21 purchased from peprotech;
14. CD3 monoclonal antibody, CD28 monoclonal antibody, CD3/CD28 magnetic bead, CD4/CD8 magnetic bead bought from a German company Miltenyi;
15. Refrigerated centrifuge bought from an American company ThermoScientific;
16. FACS bought from Thermo;
17. Fluorescence inversion microscope system bought from Olympus;
18. CD4-FITC and CD8-APC bought from BioLegend;
19. 0.9% saline solution bought from Jinmai;
20. ProteinL Magnetic Beads bought from BioVision;
21. PrimeSTAR and RetroNectin bought from Takara;
22. phycoerythrin (PE)-conjugated streptavidin bought from BD Bioscience;
23. Plasmid extraction kits and agarose gel recovery kits purchased from MN:
24. TOP 10 competent cells purchased from Tiangen;
25. NaCl, KCl, $Na_2HPO_4 \cdot 12H_2O$, $KH_2PO_4$, Trypsin, EDTA, $CaCl_2$, NaOH, PEG6000 purchased from Shanghai Sangon Biotech;
26. DNeasy kits purchased from Shanghai Generay;
27. SA-HRP purchased from Shanghai Yeasen;
28. Primers: Primers required for amplifying DNA fragments and target sites, designed by primer design principle and synthesized by a shanghai-based biotechnology company specifically as follows:

```
EF1α-F:
                                       (SEQ ID NO. 28)
5'-ATTCAAAATTTTATCGATGCTCCGGTGCCCGTCAGT-3'

EF1α-R:
                                       (SEQ ID NO. 29)
5'-TCACGACACCTGAAATGGAAGA-3'

OCTS-F:
                                       (SEQ ID NO. 30)
CATTTCAGGTGTCGTGAGGATCCGCCACCATGGCGCTGCCGGTGAC

OCTS-R:
                                       (SEQ ID NO. 31)
GGGGAGGGAGAGGGGCTTAGCGCGGCGGCAGCG

IRES-F:
                                       (SEQ ID NO. 32)
GCCCCTCTCCCTCCCCC

IRES-R:
                                       (SEQ ID NO. 33)
ATTATCATCGTGTTTTTCAAAGGAA

PDL1scab-F:
                                       (SEQ ID NO. 34)
AAAACACGATGATAATGCCACCATGAACTCCTTCTCCACAAGCC PDL1scab-R:
                                       (SEQ ID NO. 35)
AATCCAGAGGTTGATTGTCGACGAATTCTCATTTGCCCGGGCTCAG WPRE-QPCR-F:
                                       (SEQ ID NO. 36)
5'-CCTTTCCGGGACTTTCGCTTT-3'

WPRE-QPCR-R:
                                       (SEQ ID NO. 37)
5'-GCAGAATCCAGGTGGCAACA-3'

Actin-QPCR-F:
                                       (SEQ ID NO. 38)
5'-CATGTACGTTGCTATCCAGGC-3'

Actin-QPCR-R:
                                       (SEQ ID NO. 39)
5'-CTCCTTAATGTCACGCACGAT-3'
```

29. In the invention, the said DNA fragments shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27 were synthesized by Shanghai Generay Biotech Co., Ltd. in line with sequences provided by the inventor thereof.

Embodiment 1. Preparation of OCTS-CAR-T Cells

Figure 3:
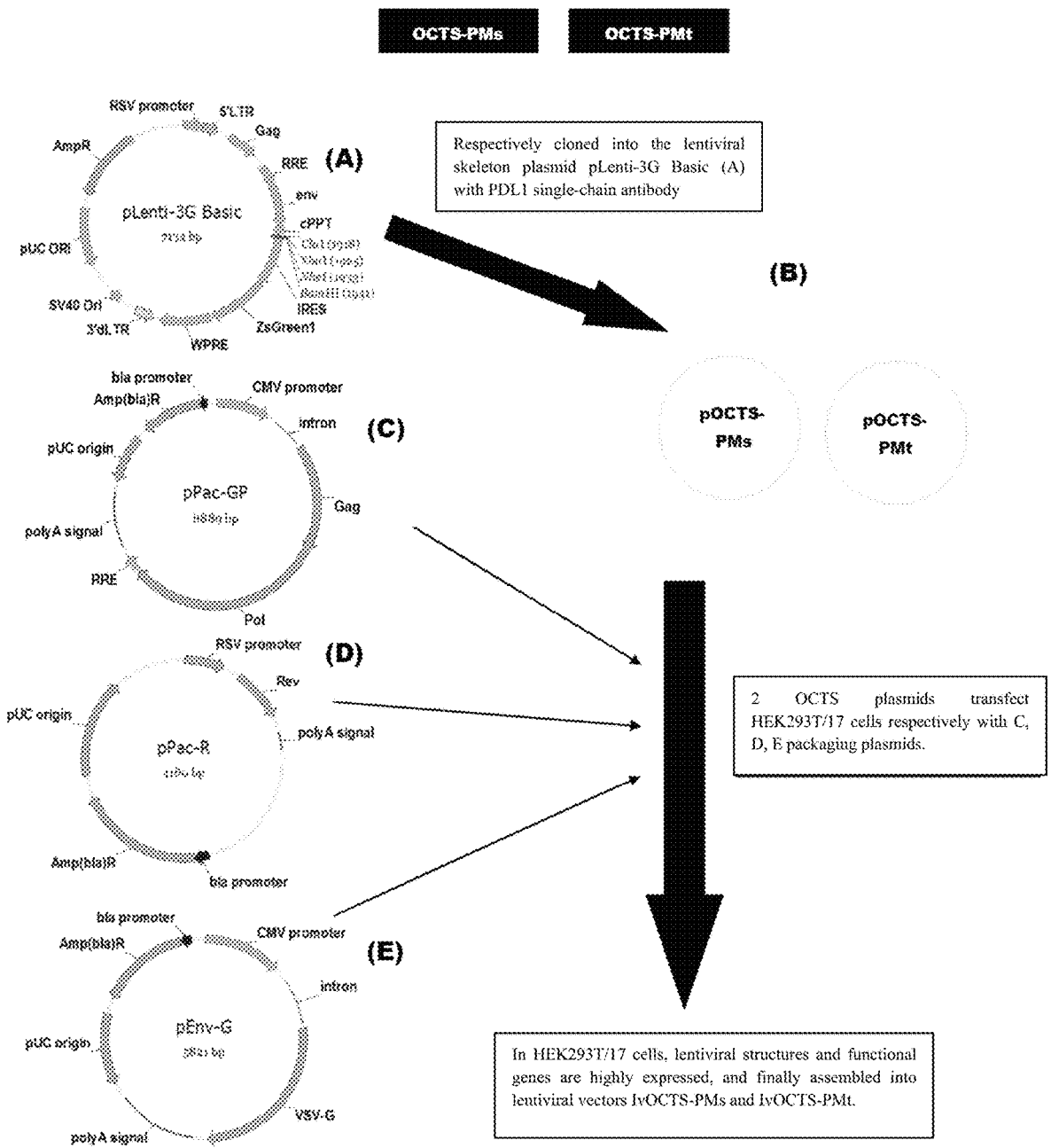
FIG. 3 is a flow chart for preparing the recombinant lentiviral vector in embodiment 1 of the invention; wherein, (A) is a schematic diagram of the structure of the lentiviral skeleton plasmid pLenti-3G basic; (B) is a schematic diagram of 2 OCTS plasmids; (C) is a schematic diagram of the structure of pPac-GP plasmid; (D) is a schematic diagram of the structure of pPac-R plasmid; (E) is a schematic diagram of the structure of pEnv-G packaging plasmid.
Figure 5A:
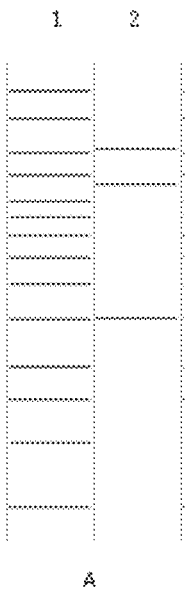
Figure 5B:
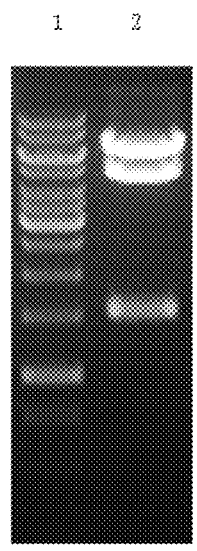
Figure 5C:
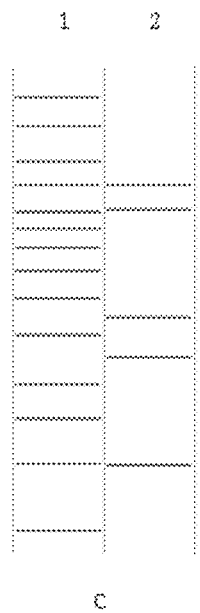
Figure 5D:
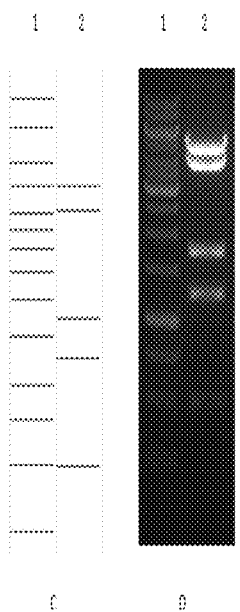

I. Methods of Preparation, Purification and Detection of Recombinant Lentiviral Vectors lvOCTS-PMs and lvOCTS-PMt The preparation method of recombinant lentiviral vectors described in the invention is as follows (see FIG. 3):

1. Combine into a design scheme for OCTS chimeric receptor the human EF1α promoter (SEQ ID NO: 14), OCTS structures [OCTS-PMs and OCTS-PMt], CD8 leader chimeric receptor signal peptide (SEQ ID NO: 15), PDL1 single-chain antibody light chain VL (SEQ ID NO: 16), PDL1 single-chain antibody heavy chain VH (SEQ ID NO: 17), mesothelin single-chain antibody light chain VL (SEQ ID NO: 18), mesothelin single-chain antibody heavy chain VH (SEQ ID NO: 19), antibody Inner-Linker (SEQ ID NO: 20), single-chain antibody Inter-Linker (SEQ ID NO: 21), CD8 Hinge chimeric receptor linker (SEQ ID NO: 22), CD8 Transmembrane chimeric receptor transmembrane domain (SEQ ID NO: 23), CD28 chimeric receptor co-stimulator (SEQ ID NO: 24), CD134 chimeric receptor co-stimulator (SEQ ID NO: 25), TCR chimeric receptor T cell activation domain (SEQ ID NO: 26), PDL1single-chain antibody (SEQ ID NO: 27), and clone the scheme into the lentiviral skeleton plasmid pLenti-3G basic by digestion, ligation and recombination to obtain recombinant lentiviral plasmids pOCTS-PMs and pOCTS-PMt respectively (see FIGS. 4A-4C for element order and No.).

(1) Conduct double digestion of the lentiviral skeleton plasmid pLenti-3G basic with Cla I and EcoR I restriction enzymes, electrophorese the product thereof on a 1.5% agarose gel to confirm the 5823 bp fragment VI, and then recover and place such gel in an Eppendorf tube, and recover corresponding fragments with the agarose gel recovery kit of MN (see Table 1) and determine the purity and concentration of the product thereof;

TABLE 1

Procedures for the recovery of agarose gel

| | | |
|---|---|---|
| 1. Sol | | Add the sol solution in a ratio of 200 μl NTI/100 mg gel, and place it in a 50° C. water bath for 5-10 minutes. |
| 7. Bind to DNA | | Centrifuge at 11,000 g for 30 seconds, and discard the filtrate. |
| 8. Wash membrane | | Add 700 μl NT3, centrifuge at 11,000 g for 30 seconds, and discard the filtrate |
| 9. Wash membrane | | Repeat step 3 once |
| 10. Dry | | Centrifuge at 11,000 g for 1 minute, replace with a new collection tube, and leave it at room temperature for 1 minute. |
| 11. Elute DNA | | Add 15-30 μl NE, leave it at room temperature for 1 minute, centrifuge at 11,000 g for 1 minute, and then collect the filtrate. |

(2) Use the primers EF1α-F and EF1α-R with the synthesized human EF1α promoter (SEQ ID NO: 14) as a template, apply the system in Table 2 on the PCR circulation conditions: 98° C. 3 min, (98° C. 10 sec, 55° C. 15 sec, 72° C. 2 min)*35 cycle, 72° C. 10 min, electrophorese the product thereof on a 1.5% agarose gel to confirm the 1208 bp fragment a, and then recover and place such gel in an Eppendorf tube, and recover corresponding fragments with the agarose gel recovery kit of MN (see Table 1) and determine the purity and concentration of the product thereof;

TABLE 2

50 μl PCR reaction system

| Reagent | Volume (μl) |
|---|---|
| H$_2$O | 32.5 |
| 5× Buffer (with Mg2+) | 10 |
| dNTP (2.5 mM each) | 4 |
| Primer1 (+)(10 μM) | 1 |
| Primer2 (−)(10 μM) | 1 |
| Template | 1 |
| PrimeSTAR | 0.5 |

(3) Use the primers OCTS-F and OCTS-R with the synthesized OCTS-PMs as a template, apply the system in Table 2 on the PCR circulation conditions: 98° C. 3 min, (98° C. 10 sec, 55° C. 15 sec, 72° C. 30 sec)*3522 cycle, 72° C. 5 min, electrophorese the product thereof on a 1.5% agarose gel to confirm the 2370 bp fragment b, and then recover and place such gel in an Eppendorf tube, and recover corresponding fragments with the agarose gel recovery kit of MN (see Table 1) and determine the purity and concentration of the product thereof;

(4) Use the primers OCTS-F and OCTS-R with the synthesized OCTS-PMt as a template, apply the system in Table 2 on the PCR circulation conditions: 98° C. 3 min, (98° C. 10 sec, 55° C. 15 sec, 72° C. 30 sec)*35 cycle, 72° C. 5 min, electrophorese the product thereof on a 1.5% agarose gel to confirm the 2382 bp fragment c, and then recover and place such gel in an Eppendorf tube, and recover corresponding fragments with the agarose gel recovery kit of MN (see Table 1) and determine the purity and concentration of the product thereof;

(5) Use the primers IRES-F and IRES-R with the synthesized IRES ribosome binding sequence (SEQ ID NO: 12) as a template, apply the system in Table 2 on the PCR circulation conditions: 98° C. 3 min, (98° C. 10 sec, 55° C. 15 sec, 72° C. 30 sec)*35 cycle, 72° C. 5 min, electrophorese the product thereof on a 1.5% agarose gel to confirm the 575 bp fragment d, and then recover and place such gel in an Eppendorf tube, and recover corresponding fragments with the agarose gel recovery kit of MN (see Table 1) and determine the purity and concentration of the product thereof;

(6) Use the primers PDL1scab-F and PDL1 scab-R with the synthesized PDL1 single-chain antibody (SEQ ID NO: 27) as a template, apply the system in Table 2 on the PCR circulation conditions: 98° C. 3 min, (98° C. 10 sec, 55° C. 15 sec, 72° C. 30 sec)*35 cycle, 72° C. 5 min, electrophorese the product thereof on a 1.5% agarose gel to confirm the 2355 bp fragment c, and then recover and place such gel in an Eppendorf tube, and recover corresponding fragments with the agarose gel recovery kit of MN (see Table 1) and determine the purity and concentration of the product thereof;

(7) Add combinations of recombinant lentiviral plasmid DNA fragments into the Eppendorf tubes with a total volume of 5 μL and at a molar ratio of 1:1:1; add 15 μL homologous recombinant enzyme reaction solution into the tubes, mix and incubate them at 42° C. for 30 minutes, and put the tubes on ice for 2-3 minutes; add the reaction solution into 50 μL TOP10, rotate the tubes gently to mix the contents, place the tubes in ice for 30 minutes, put the tubes in a constant temperature water bath pot preheated to 42° C. for 90-second heat shock, quickly transfer the tubes to the ice bath, and cool the cells for 2-3 minutes; add 900 μl LB culture medium into each tube, transfer the tubes to a shaking bed at 37° C., and incubate the tubes for 1 hour to resuscitate the bacteria; take 100 μL transformed bacteria solution, coat it on the Amp LB agar plate, invert the flat dish, and put it in a constant temperature incubator at 37° C. for 16-hour cultivation.

TABLE 3

Combination of recombinant lentiviral plasmid DNA fragments

| Recombinant lentiviral plasmid | Combination of fragments |
|---|---|
| pOCTS-PMs | a, b, d, e |
| pOCTS-PMt | a, c, d, e |

Select clones for colony PCR identification, among which those identified as correct are exactly recombinant lentiviral plasmids pOCTS-PMs and pOCTS-PMt, conduct enzyme digestion identification of correct clones (see FIGS. 5A-5D), and send the sequencing review results.

2. Packaging of Recombinant Lentiviral Vectors lvOCTS-PMs and lvOCTS-PMt (1) Complete medium: take out the pre-heated fresh medium, add 10% FBS+5 ml Pen-Srep, and mix them upside down;

(2) 1×PBS solution: weigh 8 g of NaCl, 0.2 g of KCl, 3.58 g of Na$_2$HPO$_4$.12H$_2$O, 0.24 g of KH$_2$PO$_4$, and put them in a 1000 ml beaker, and add 900 ml of Milli-Q grade ultrapure water to dissolve. After completion of the dissolution, the volume was adjusted to 1000 ml using a 1000 ml measuring cylinder, and the mixture was sterilized by heat sterilization at 121° C. for 20 minutes;

(3) 0.25% Trypsin solution: weigh 2.5 g of Trypsin, 0.19729 g EDTA, and put them in a 1000 ml beaker, and add 900 ml of 1×PBS solution to dissolve. After completion of the dissolution, the volume was adjusted to 1000 ml using a 1000 ml measuring cylinder, and the mixture was sterilized via 0.22 μM filter. It could be saved in the refrigerator at −20° C. for long-term use;

(4) 0.5 M $CaCl_2$) solution: weigh 36.75 g of $CaCl_2$, and dissolve it with 400 ml of Milli-Q grade ultrapure water; The volume was adjusted to 500 ml with Milli-Q grade ultrapure water, and mixed; the mixture was sterilized via 0.22 μM filter, and stored in 50 ml centrifuge tubes with about 45 ml in each tube at 4° C.;

(5) 2×HBS solution: weigh 4.09 g of NaCl, 0.269 g of $Na_2HPO_4$, 5.96 g of Hepes, and dissolve them with 400 ml Milli-Q grade ultrapure water; After calibrating the pH meter, the pH of the HBS solution was adjusted to 7.05 with 2 M NaOH solution. It was about 3 ml of 2 M NaOH to consume to adjust the pH of each bottle of HBS;

(6) The frozen HEK293T/17 cells were removed from the liquid nitrogen container and rapidly transferred to a 37° C. water bath for 1-2 minutes, and then put them on a super clean bench. Aseptically transfer all the liquid in the freezing tube to a 10 $cm^2$ petri dish, and make up DMEM containing 10% FBS to 8 mL/10 $cm^2$ dish, and observe the cells under microscope after 24 hours. Passage was performed with the degree of cell confluence greater than 80%;

(7) HEK293T/17 cells with good cell status and no pollution were selected, and each 2-6 petri dishes were used as a group. After trypsinizing the cells, 4-12 ml of complete medium was pipetted with an electric pipette to add 2 ml to each digested dish to avoid drying the dish; all cells were isolated into single cell suspensions using a 1 ml pipette and transferred to medium bottles;

(8) The remaining cells in the above 2-6 petri dishes were transferred to the medium bottles, and the petri dishes were rinsed with the medium again;

(9) Close the cap of the medium bottles and turn them upside down for about 10 times to fully mixed the cell suspension. Transfer the cells to 8-24 10 $cm^2$ petri dishes. For each dish, there shall be about $4\times10^6$ cells/10 ml complete medium. If the cell density is significantly different from the expected, the number of cells is required to be counted, and then the cells will be inoculated according to the quantity of $4\times10^6$ per dish;

(10) Arrange each of the 6 petri dishes into a pile, and keep the fit between the upper and lower dishes. Shake the petri dishes left and right, back and forth several times to make cells fully spread out, and then put them into an incubator with 5% $CO_2$. The remaining cells were treated as the same;

(11) Upon Checking the passage cells, the cells shall be at 70-80% confluence, with full contour, good attachment and even distribution in petri dishes;

(12) For changing the solution, the medium was replaced with fresh complete medium with 9 ml per dish. The $CO_2$ concentration of incubator was increased to 8%;

(13) To prepare DNA/$CaCl_2$ according to N+0.5. The amount of HEK293T/17 cell transfection plasmid per dish was used in the following ratios: recombinant lentiviral plasmid (20 μg), pPac-GP (15 μg), pPac-R (10 μg), pEnv-G (7.5 μg). Take a new 5 ml centrifuge tube, add 0.5 M $CaCl_2$: 0.25 ml, recombinant lentiviral plasmid 20 μg: pPac-GP 15 μg: pPac-R 10 μg: pEnv-G 7.5 μg, supplement ultrapure water to 0.5 ml, and cover the cap to mix them fully;

(14) Take another 5 ml centrifuge tube and add 0.5 ml DNA/$CaCl_2$) solution. Open a vortex mixer, hold the upper end of the 5 ml centrifuge tube with one hand, and make the bottom of the tube contact the oscillation chamber, so that the liquid could spread on the tube wall. Take a 1 ml pipette with anther hand to suck 0.5 mL 2×HBS solution, add it into the centrifuge tube slowly and control the flow velocity. It was advisable to complete the drip in half a minute. After 2×HBS was added, it should be oscillated for another 5 seconds, and then stop oscillating. It could be directly added into the cells that need transfection;

(15) Take a dish of cells and drop 1 mL calcium transfection solution in the centrifuge tube in the dish to distribute the calcium transfection solution throughout the petri dish as much as possible;

(16) After the calcium transfection solution was added, the petri dish was marked on the cover, and put back in another incubator with 5% $CO_2$. Make sure that the petri dish was placed horizontally, and that there were no more than 6 petri dishes in each pile. These dishes were placed in the incubator with 5% $CO_2$ for 6-8h;

(17) The $CO_2$ concentration of the first incubator was adjusted at 5%;

(18) The cells status was check 24 hours later. The cell confluence should be around 80-85% and in good condition. Aspirate the medium and replace 10 ml of fresh DMEM complete medium;

(19) The transfection efficiency was observed 48 hours later. Most cells were still adherent. It could be seen that more than 95% of the cells would have green fluorescence. The supernatant of the same virus packaging was collected together, and 10 mL of fresh medium was added to the petri dish;

(20) The same virus supernatant was collected again 72 hours later. The two collections were put together, and the petri dishes were discarded; the supernatant collected at this time contained the recombinant lentiviral vectors lvOCTS-PMs and lvOCTS-PMt.

3. Purification of Recombinant Lentiviral Vectors by Ion Exchange Chromatography (1) The collected supernatant was filtered through a 0.22 μm-0.8 μm PES filter using a Thermo vacuum pump to remove impurities;

(2) 1.5 M NaCl 250 mM Tris-HCl (PH6-8) was added to the supernatant at a ratio of 1:1 to 1:10;

(3) Two ion exchange columns were placed in series, and they were passed through sequentially by 4 ml 1 M NaOH, 4 ml 1 M NaCl, 5 ml 0.15 M NaCl 25 mM Tris-HCl (pH 6-8) solution;

(4) The solution obtained in step 2 was pumped into the ion exchange column with a peristaltic pump at a rate of 1-10 m/min (5) After all the supernatant was passed through the column, it was washed with 10 ml of 0.15 M NaCl 25 mM Tris-HCl (pH 6-8) solution;

(6) According to the sample size, 1-5 ml of 1.5 M NaCl 25 mM Tris-HCl (pH 6-8) was used for elution and the eluate was collected; and (7) The eluate was divided into tubes about 25 to 50 μl each, and stored in a refrigerator with −80° C. for long-term storage.

4. Titre Determination of Recombinant Lentiviral Vectors (1) 293T cells were inoculated with 24-well plates. The number of cells in each well was $5\times10^4$, and the volume of medium added was 500 μL. As the growth rate of different types of cells was different, the rate of cell fusion during viral infection was 40%-60%;

(2) Three sterile EP tubes were prepared, and 90 μL fresh complete medium (high glucose DMEM+10% FBS) was added into each tube to inoculate the cells. 24 hours later, the cells in the two pores were taken and counted with a hemocytometer to determine the actual number of cells at the time of infection, denoted as N;

(3) 10 μL of the virus stock to be determined was added to the first tube. After gently mixing, 10 μL of the virus stock was added to the second tube, and then sequentially operated until the last tube; 410 μL complete medium (high glucose DMEM+10% FBS) was added into each tube, and the final volume was 500 μL;

(4) 20 hours after the infection, the cultural supernatant was removed and replaced with 500 μL complete medium (high glucose DMEM+10% FBS). The cells were continuously cultured for 48 hours in 5% $CO_2$;

(5) After 72 hours, the fluorescence expression was observed. Under normal circumstances, the number of fluorescence cells decreased with the increase of dilution ratio. At the same time, photos were taken;

(6) The cells were digested with 0.2 ml 0.25% trypsin-EDTA solution, and then they were placed at 37° C. for 1 minute. The whole cellular surface were purged with medium, and the cells were collected by centrifugation. Genomic DNA was extracted according to the instructions of DNeasy kit. 200 μL of eluent were added to each sample tube to remove DNA, and then they were quantified, (7) The DNA detection qPCRmix manifold I was prepared (QPCR primer sequences were SEQ ID NO: 36-SEQ ID NO: 37):

| | |
|---|---|
| 2× TaqMan Master Mix | 25 μl × n |
| Forward primer (100 pmol ml-1) | 0.1 μl × n |
| Reverse primer (100 pmol ml-1) | 0.1 μl × n |
| Probe (100 pmol ml-1) | 0.1 μl × n |
| $H_2O$ | 19.7 μl × n | n=number of reactions. For example, the total n were 40. 1 ml of 2× TaqMan Universal PCR Master Mix, 4 μl of forward primer, 4 μl of reverse primer, 4 μL of probe and 788 μL of $H_2O$ were mixed and placed on ice after being shaken;

(8) The reference DNA detection qPCRmix manifold II were prepared (QPCR primer sequences were SEQ ID NO: 38-SEQ ID NO: 39):

| | |
|---|---|
| 2× TaqMan Master Mix | 25 μl × n |
| 10× RNaseP primer/probe mix | 2.5 μl × n |
| $H_2O$ | 17.5 μl × n | n=number of reactions. For example, the total n were 40. 1 ml of 2× TaqMan Universal PCR Master Mix, 100 μL pf 10×RNaseP primer/probe mix and 700 μL of $H_2O$ were mixed and placed on ice after being shaken;

(9) The PCR system was established on a pre-cooled 96-well PCR plate. Take 45 μL from each tube of manifold I to add to the wells of each row of A-D. Take 45 μL from each tube of manifold II to add to the wells of each row of E-G.

(10) 5 μL of the standard plasmid and the genomic DNA from the samples to be tested were taken respectively to add to the A-D row, and each sample was repeated once. 1 well was left to add 5 μL of water as no-template control.

(11) 5 μl of the genomic standards and the genomic DNA from the samples to be tested were taken respectively to add to the E-G row, and each sample was repeated once. 1 well was left to add 5 μL of water as no-template control.

(12) The quantitative PCR instrument used was the ABI PRISM 7500 quantitative system. The cyclic conditions were set to: 50° C. 2 min, 95° C. 10 min, (95° C. 15 sec, 60° C. 1 min)×40 cycle.

Data analysis: the copy number of lentiviral vectors integrated in the measured DNA samples was calibrated with the number of genomes to obtain the copy number of viruses integrated in each genome.

The calculation formula of integration units per ml (IU $ml^{-1}$) was as follows:

$$IU\ ml^{-1}=(C\times N\times D\times 1000)/V$$

wherein: C=the average virus copy number per genome integration

N=number of cells at the time of infection (approximately $1\times 10^5$)

D=dilution of the viral vector

V=the volume of diluted virus added

Figure 6:
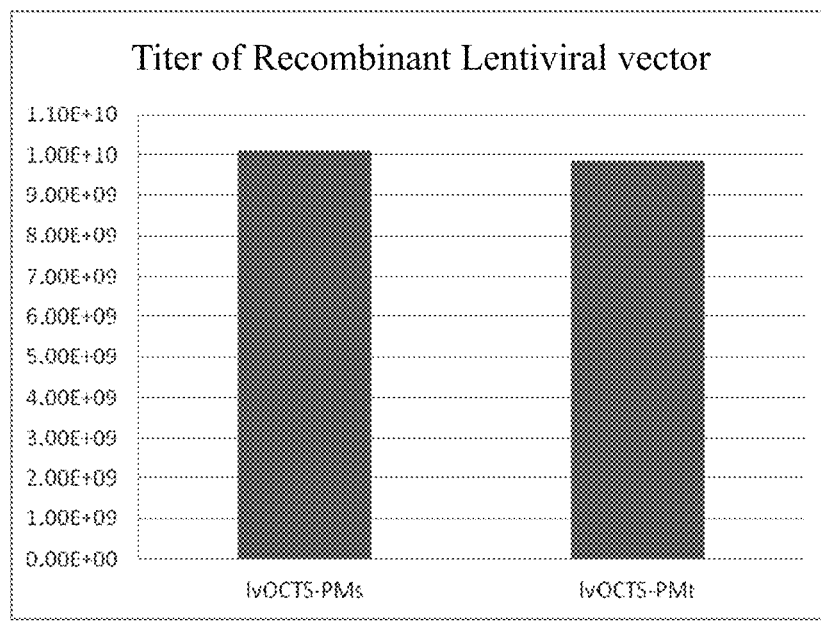
FIG. 6 is a schematic diagram of titer detection results of recombinant lentiviral vectors in embodiment 1 of the invention.

(13) Titer results of recombinant lentiviral vectors lvOCTS-PMs and lvOCTS-PMt (see FIG. 6).

II. Preparation of OCTS-CAR-T Cell

Figure 7:
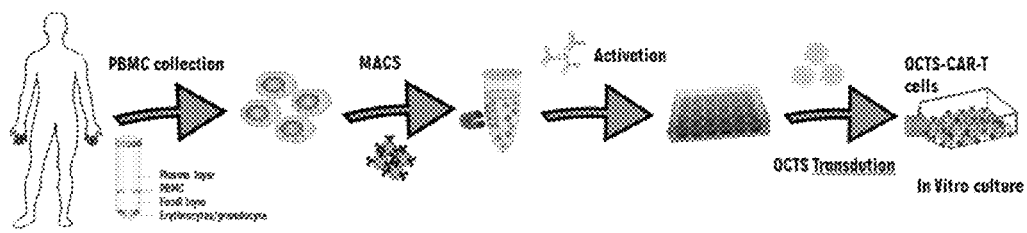
FIG. 7 is the flow diagram of the steps of preparing OCTS-CAR-T cells said in embodiment 1 of the invention, involving isolated culture, activation, gene transduction, OCTS-CAR-T cell identification and other stages.
Figure 9B:
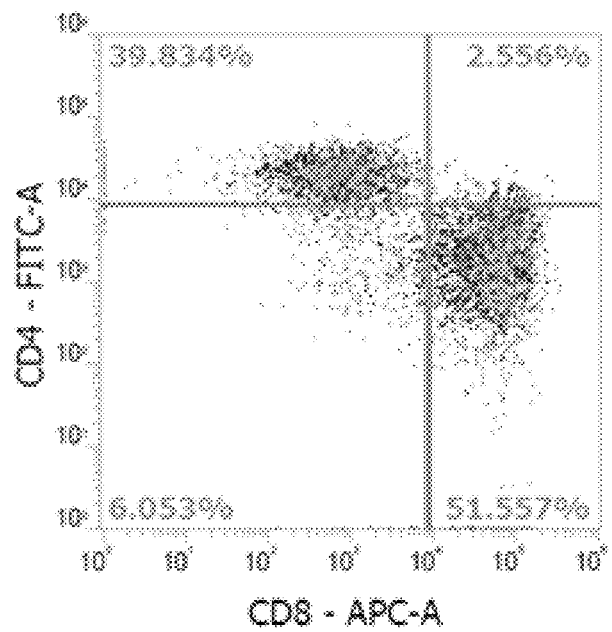
Figure 9C:
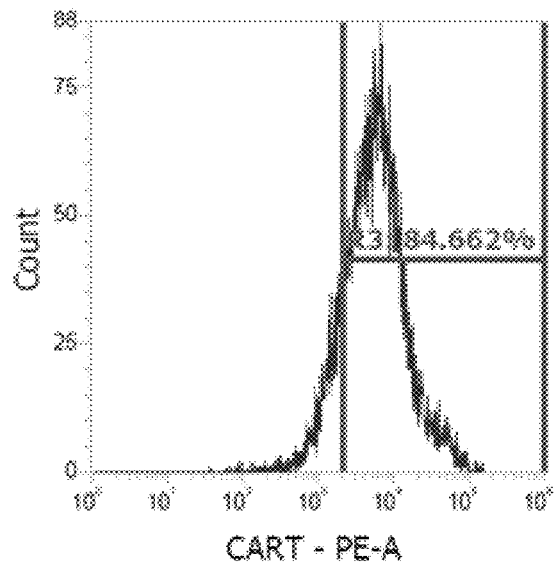
Figure 9D:
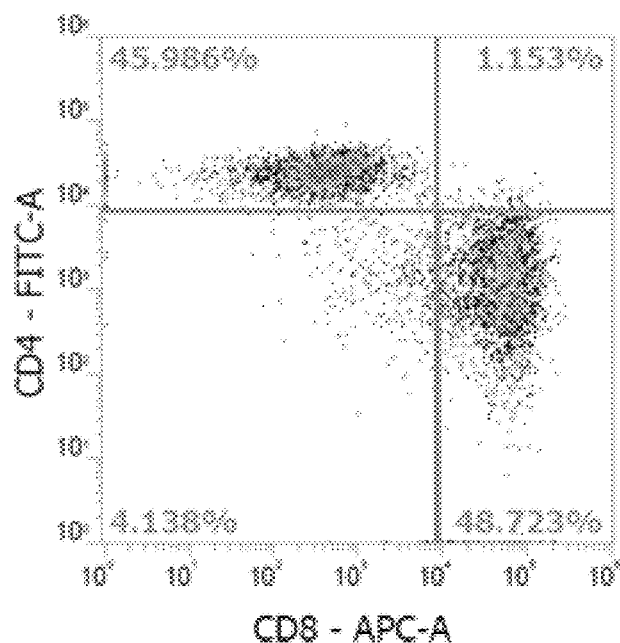

Preparation method of the OCTS-CAR-T cell described in the invention is as below (see FIG. 7):

1. PBMC Separation (1) Draw 50 ml fresh peripheral blood from healthy donors;

(2) Spray ethyl alcohol onto the blood collecting bag twice and wipe it off;

(3) Draw blood cells out of the bag with a 50 ml injector and transfer them to a new 50 ml tube;

(4) Centrifuge the tube at 400 g, 20° C. for 10 min;

(5) Transfer upper blood plasma into a new 50 ml centrifuge tube, inactivate the blood plasma at 56° C. for 30 min, centrifuge the tube at indoor temperature, 2000 g for 30 min, and take and put the supernatant into a 50 ml centrifuge tube for later use;

(6) Add D-PBS(-) into the tube until the volume of the solution in it reaches 50 ml, tighten up the cap, and overturn the tube for mixing the solution in it;

(7) Take 2 new 50 ml centrifuge tubes, and add 15 ml Ficoll into each of them;

(8) Carefully add 25 ml blood cell diluent into the Ficoll in each tube, and centrifuge the tubes at 800 g, 20° C. for 20 min;

(9) There are four layers of liquid in the centrifuge tubes, which from top to bottom are yellow blood plasma layer (recovered for later use), albuginea, water white Ficoll, red and black mixed cells;

(10) Carefully draw the albuginea into a new 50 ml centrifuge tube, add D-PBS(-) into the tube until the volume of the solution in it reaches 50 ml, overturn the tube for mixing the solution in it, and centrifuge the tube at 500 g, 20° C. for 10 min;

(11) Add 25 ml 5% human serum albumin, resuspend cells, and centrifuge the tube at 400 g, 20° C. for 10 min;

(12) Remove the supernatant, add 25 ml 5% human serum albumin, resuspend cells until they are precipitated, and count after getting them through the 70 um screen mesh; and

(13) Take a portion of cell suspension containing $1.25\times 10^8$ cells for activation, centrifuge the remaining cell suspension at 400 g, 20° C. for 10 min, add CryoPremium into and freeze it.

2. CD4/CD8 Positive T Cell Sorting (1) Count obtained PBMCs, add sorting buffer solution in the ratio of 80 μL/$10^7$ cells, and resuspend cells until they are precipitated;

(2) Add CD4/CD8 magnetic beads in the ratio of 20 μL/$10^7$ cells, and incubate the solution at 4° C. for 15 min after blowing and mixing it;

(3) Take magnetic beads out of the cell mixture, add sorting buffer solution into it in the ratio of 2 ml/$10^7$ cells, overturn and mix it, and centrifuge it at 250 g, 4° C. for 10 min; (4) Add sorting buffer solution in the ratio of 500 μL/10s cells, and resuspend cells until they are precipitated;

(5) Clamp the LS separation column onto the magnetic shelf with tweezers;

(6) Prepare 2 15 ml centrifuge tubes at the same time, and mark them CD4−/CD8−cell sap (tube A) and CD4+/CD8+ cell sap (tube B) respectively;

(7) Rinse LS with 3 ml separation buffer solution, and use tube A to collect the buffer solution;

(8) Add the cell-magnetic bead mixture, and then 3 ml buffer solution to wash the column three times (new liquid is added when there is no liquid residue), and collect obtained CD4/CD8-cells;

(9) Separate the LS separation column from the magnetic shelf, use tube B to collect cell suspension, add 5 ml buffer solution, wash the column together with the inner plunger thereof a little harder, collect CD4+/CD8+cells, take samples from them and count the samples; and

(10) Resuspend cells until they are precipitated with AIM-V medium according to the cell density of $1\times10^6$/ml-$4\times10^4$/ml, and add $2\times10^5$-$10^6$ U/L IFN-γ factors.

3. Activation of T Cells (1) Add into a 24-pore plate one day in advance the $1\text{-}10^3$ ug/L-$1\times10^4$ ug/L CD3 monoclonal antibody and $1\times10^3$ ug/L-$1\times10^4$ ug/L CD28 monoclonal antibody, seal it with sealing film, and coat it overnight at 4° C.; and (2) Take out the coated T75 bottle, discard the coating buffer, and wash it with D-PBS(−) once; inject the cell suspension obtained by sorting into a T75 bottle, share it up, and put it in an incubator at 37° C., 5% $CO_2$ for culture;

4. CAR Gene Transduction and OCTS-CAR-T Cell Induction Culture (1) Cost $1\times10^3$ ug/L-$1\times10^4$ ug/L RetroNectin in a 24-pore plate one day in advance, seal it with sealing film, and coat it overnight at 4° C.; and (2) Add lentiviral transgenic vectors lvOCTS-PMs and lvOCTS-PMt into the 24-pore plate according to $5\times10^5$ cells for each pore and MOI=5-20 along with AIM-V medium containing $2\times10^5$-$5\times10^5$ U/L rIL-2, $5\times10^3$ ng/L-$1\times10^4$ ng/L rIL-7, $5\times10^3$ ng/L-$1\times10^4$ ng/L rIL-15, $5\times10^3$ ng/L-$1\times10^4$ ng/L rIL-21 and 10% autoserum for continuous culture at 37° C., 5% $CO_2$.

5. In-Vitro Expansion of OCTS-CAR-T Cells (1) Add the same amount of AIM-V medium containing $2\times10^5$-$5\times10^5$ U/L rIL-2, $5\times10^3$ ng/L-$1\times10^4$ ng/L rIL-7, $5\times10^3$ ng/L-$1\times10^4$ ng/L rIL-15, $5\times10^3$ ng/L-$1\times10^4$ ng/L rIL-21 and 10% autoserum every 2 days, keep PH within 6.5-7.5 and cell density within $5\times10^5$-$2\times10^6$/ml, and continue to culture it at 37° C., 5% $CO_2$ for 10-14 days; and (2) Use the frozen and cultured OCTS-CAR-T cells for subsequent detection on the 7$^{th}$ day or so.

Embodiment 2. OCTS-CAR-T Cell Pathogen Detection and Expression Detection

I. Endotoxin Determination (1) The working standard of endotoxin was 15 EU per dose;

(2) Sensitivity of Tachypiens Amebocyte Lysate (TAL) λ=0.25 EU/ml, 0.5 ml/tube (3) Dilution of endotoxin standard: take one endotoxin standard, dilute it into 4λ and 2λ solution with BET water, seal with sealing film and vortex for 15 min; During dilution, each dilution step should be mixed on the vertex mixer for 30 s;

(4) Adding samples: Several TAL were taken, each was dissolved in 0.5 ml of BET water, and then divided into several endotoxin-free tubes (0.1 ml each tube). Two of them were negative control which were added 0.1 ml of BET water to each of them;

Two tubes were used for positive control which were added 0.1 ml endotoxin working standard solution with concentration of 2λ to each of them;

Two tubes were used for positive control of sample which were added 0.1 ml sample solution contained 2λ endotoxin standard (1 ml of 20× dilution of sample to be tested+1 ml of solution contained 4λ endotoxin standard=2 ml of 40× dilution of sample contained 2λ endotoxin standard).

0.1 ml sample was added into the sample tube at the dilution rate shown in Table 4 and with 37±1° C. water bath (or incubator) and heat preservation for 60±1 min;

TABLE 4

Dilution ratio of endotoxin and corresponding endotoxin content

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |
| Results | | | | | | | |

(5) According to the endotoxin detection results of OCTS-CAR-T cells (as shown in Table 5), the content of endotoxin in all cells was less than 2.5 EU/ml, meeting the standard in the Pharmacopoeia of the People's Republic of China, which is less than 10 EU/ml;

TABLE 5

| Dilution Multiple | Original Fluid | 5 | 10 | 20 | 40 | 80 | 160 |
|---|---|---|---|---|---|---|---|
| Corresponding EU/ml | 0.25 | 1.25 | 2.5 | 5 | 10 | 20 | 40 |
| OCTS-PMs-CAR-T | (+) | (−) | (−) | (−) | (−) | (−) | (−) |
| OCTS-PMt-CAR-T | (+) | (+) | (−) | (−) | (−) | (−) | (−) |

II. Detection of Mycoplasma (1) Three days before the experiment, the cell samples were cultured in antibiotic-free medium:

(2) 1 ml cell suspension (more than $1*10^5$ cells) was collected and placed in a 1.5 ml centrifugal tube;

(3) Centrifuge at 13,000 g for 1 min, collect sediment and discard culture medium;

(4) Add 500 μL PBS, blowing or whirlpool oscillation with the gun head, and resuspend sediment. Centrifuge for 5 min at 13,000 g;

(5) Repeat step (4) once;

(6) Add 50 μL Cell Lysis Buffer, blow and suck with gunhead, mix well, and incubate in water bath at 55° C. for 20 minutes;

(7) The samples were heated at 95° C. for 5 minutes;

(8) After centrifugation at 13,000 g for 5 min, 5 μL supernatant was used as template. The 25 μL PCR reaction system was ddH20 6.5 μL, Myco Mix 1 μL, 2× Taq Plus Mix Master (Dye Plus) 12.5 μL and template 55 μL. The cycle conditions of PCR were 95° C. 30 sec, (95° C. 30 sec, 56° C. 30 sec, 72° C. 30 sec)*30 cycle and 72° C. 5 min; and (9) According to the mycoplasma detection results (as shown in FIG. 8), the OCTS-CAR-T cells contained no mycoplasma.

III. OCTS Gene Transduction Efficiency Detection and Immunophenotyping Detection (1) Collect T cells transduced by virus, resuspend cells with D-PBS(−) solution containing 1-4% human serum albumin, and adjust the ratio to 1×10⁶/ml;

(2) Add D-PBS(−) solution containing 1-4% human serum albumin into a centrifuge tube, mix it, centrifuge it at 350 g for 5 min, and discard the supernatant;

(3) Repeat step (2) once;

(4) Resuspend cells with 0.2 ml D-PBS(−) solution containing 1-4% human serum albumin, add into the centrifuge tube 1 μL 1 mg/μL protein L, 5 μL CD4–FITC and 5 μL CD8–APC, mix it, and incubate it at 4° C. for 45 min;

(5) Add into the centrifuge tube 1 ml D-PBS(−) solution containing 1-4% human serum albumin, mix it, centrifuge at 350 g for 5 min and discard the supernatant;

(6) Repeat step (5) twice;

(7) Resuspend cells with 0.2 ml D-PBS(−) solution containing 1-4% human serum albumin, add 0.2 μL PE-SA into the centrifuge tube, mix it, and incubate it at 37° C. in dark for 15 min;

(8) Add into the centrifuge tube 1 ml D-PBS(−) solution containing 1-4% human serum albumin, mix it, centrifuge at 350 g for 5 min and discard the supernatant;

(9) Resuspend cells with 1 ml D-PBS(−) solution until they are precipitated, centrifuge at 350 g for 5 min and discard the supernatant;

(10) Repeat step (9) twice;

(11) Resuspend cells with 0.4 ml D-PBS(−) solution until they are precipitated, and detect the cells with FACS; and

(12) According to the results of OCTS gene transduction efficiency detection and immunophenotyping detection shown in FIGS. 9A-9D, the efficiency of infection of most prepared OCTS-CAR-T cells were within 30%-40%, and the ratio of CD4 positive cells to CD8 positive cells was within 1:3-3:1, meaning subsequent function detection can be carried out.

Embodiment 3. Functional Detection of OCTS-CAR-T Cell

I. Evaluation of Killing Effect on Target Cells (1) Respectively culture target cells [PDL1⁺K562, ⁺K562, PDL1⁺MESOTHELIN⁺K562, K562 cells] and effector cells [OCTS-CAR-T cells];

(2) Collect target cells 4×10⁵ cells and OCTS-CAR-T cells 2.8×10⁶ cells, centrifuge them at 800 g for 6 min, and discard the supernatant;

(3) Respectively resuspend target cells and effector cells with 1 ml D-PBS(−), centrifuge them at 800 g for 6 min, and discard the supernatant;

(4) Repeat step (3) once;

(5) Resuspend effector cells with 700 μL medium (AIM-V medium+1-10% FBS), and target cells with 2 ml medium (AIM-V medium+1-10% FBS);

(6) Set up the experimental pores with the multiplicity of infection of 1:1, 5:1 and 10:1, and control groups (K562 cells) with 3 compound pores each. Grouping of co-incubation of effector cells respectively with single target cells and double target cells is shown in Table 6;

TABLE 6

| Effector Cell | Target Cell 1 | Target Cell 2 | Target Cell 3 |
|---|---|---|---|
| OCTS-PMs-CAR-T | PDL1⁺ K562 | MESOTHELIN⁺ K562 | PDL1⁺ MESOTHELIN⁺ K562 |
| OCTS-PMt-CAR-T | PDL1⁺ K562 | MESOTHELIN⁺ K562 | PDL1⁺ MESOTHELIN⁺ K562 |

Figure 10:
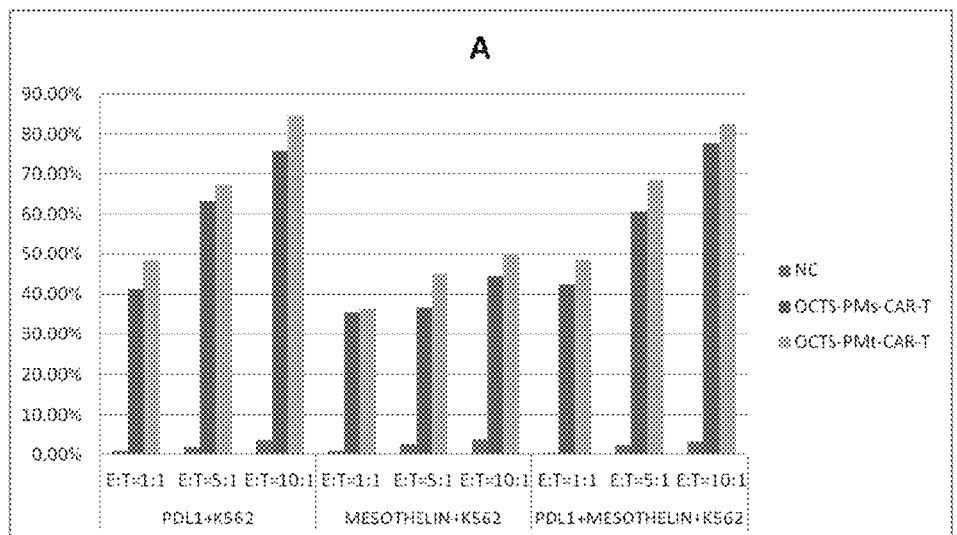
FIG. 10 is a schematic diagram of the comparison in terms of killing effect on different target cells between OCTS-PMs-CAR-T cell and OCTS-PMt-CAR-T cell on different multiplicity of infection conditions in embodiment 3 of the invention.

(7) Plate centrifugation at 250 g for 5 min;

(8) Culture it in an incubator at 37° C., 5% $CO_2$ for 4 hours, (9) Plate centrifugation at 250 g for 5 min;

(10) Take 50 μL supernatant from each pore to a new 96-pore plate, and add 50 μL substrate solution to each pore (in dark);

(11) Incubate it in dark for 25 min;

(12) Add 50 μL stop buffer into each pore;

(13) Detect 490 nm absorbance with microplate reader;

(14) Average the three compound pores; reduce the light absorption value of all experimental pores, target cell pores and effector cell pores by the average light absorption value under the background of medium; reduce the maximum light absorption value of target cells by the average volume correction control light absorption value;

(15) Bring the corrected values obtained in step (14) into the following formula to calculate the percentage of cytotoxicity produced by each multiplicity of infection. According to the results shown in FIG. 10, OCTS-CAR-T cells have better killing effect on their own single target cells and double target cells, and the killing efficiency of CAR-T cells with Turn OCTS structure is lightly higher than that of CAR-T cells with Series OCTS structure;

Killing efficiency=(Experimental pore−Effector cell pore−Target cell pore)/(Maximum target cell pore−Target cell pore)×100%

(16) Such experimental results show that OCTS structure formed by modifying the antigen recognition domain in traditional CAR structure can significantly improve the scope of recognition and killing target cells of OCTS-CAR-T cells, and thus OCTS-CAR-T cells will play a huge role in future cellular therapy of pancreatic cancer, malignant mesothelioma and other mesothelin positive/PDL1positive/both mesothelin and PDL1 positive malignant tumors.

What is claimed is:

1. An OCTS-based CAR-T vector for targeting malignant tumors expressing mesothelin, PDL1, or both of the mesothelin and the PDL1, comprising: a lentiviral skeleton plasmid, a human EF1α promoter, a first nucleotide sequence of a one CAR with two ScFvs (OCTS) chimeric receptor structural domain, and a second nucleotide sequence encoding a programmed cell death receptor ligand 1 (PDL1) single-chain antibody; wherein
the lentiviral skeleton plasmid comprises:
an AmpR sequence containing an ampicillin resistance gene for a vast expansion of a target bacterial strain, wherein the AmpR sequence is shown in SEQ ID NO: 1;
a prokaryotic replicon pUC Ori sequence for plasmid replication, wherein the prokaryotic replicon pUC Ori sequence is shown in SEQ ID NO: 2;
a viral replicator SV40 Ori sequence for enhancing replication in eukaryotic cells, wherein the viral replicator SV40 Ori sequence is shown in SEQ ID NO: 3;
a lentiviral packaging cis-element for lentiviral packaging;
a third nucleotide sequence encoding ZsGreen1 green fluorescent protein, wherein the third nucleotide sequence is shown in SEQ ID NO: 11,
an internal ribosome entry site (IRES) ribosome binding sequence, wherein the IRES ribosome binding sequence is shown in SEQ ID NO: 12; and
an eWPRE enhanced marmot hepatitis B virus post-transcriptional controlling element for enhancing transgenic expression efficiency, wherein the eWPRE enhanced marmot hepatitis B virus post-transcriptional controlling element is shown in SEQ ID NO: 13;
a sequence of the human EF1αpromoter is shown in SEQ ID NO: 14;
the first nucleotide sequence of the OCTS chimeric receptor structural domain comprises:
a fourth nucleotide sequence encoding a cluster of differentiation 8 (CD8) leader chimeric receptor signal peptide, as shown in SEQ ID NO: 15,
a fifth nucleotide sequence encoding a first PDL1 single-chain antibody light chain, as shown in SEQ ID NO: 16,
a sixth nucleotide sequence encoding a second PDL1 single-chain antibody heavy chain, as shown in SEQ ID NO: 17,
a seventh nucleotide sequence encoding a first mesothelin single-chain antibody light chain, as shown in SEQ ID NO: 18,
an eighth nucleotide sequence encoding a second mesothelin single-chain antibody heavy chain, as shown in SEQ ID NO: 19,
a ninth nucleotide sequence encoding an antibody Inner-Linker, as shown in SEQ ID NO: 20,
a tenth nucleotide sequence encoding a single-chain antibody Inter-Linker, as shown in SEQ ID NO: 21,
an eleventh nucleotide sequence encoding a CD8 hinge chimeric receptor linker, as shown in SEQ ID NO: 22,
a twelfth nucleotide sequence encoding a CD8 transmembrane chimeric receptor transmembrane domain, as shown in SEQ ID NO: 23,
a thirteenth nucleotide sequence of a chimeric receptor T cell activation domain of T cell receptor (TCR), as shown in SEQ ID NO: 26, and
a fourteenth nucleotide sequence of a chimeric receptor co-stimulator domain; wherein the chimeric receptor co-stimulator domain is at least one selected from the group consisting of 4-1BB, ICOS, CD27, OX40 (CD134), CD28, MYD88, IL1R1, CD70, TNFRSF19L, TNFRSF27, TNFRSF1OD, TNFRSF13B, and TNFRSF18.

2. The OCTS-based CAR-T vector of claim 1, wherein, the lentiviral packaging cis-element employs a second-generation lentiviral vector or a third-generation lentiviral vector; wherein
the second-generation lentiviral vector comprises:
a lentiviral 5 terminal long terminal repeat (LTR), as shown in SEQ ID NO: 5,
a lentiviral 3 terminal Self-Inactivating LTR, as shown in SEQ ID NO: 6,
a Gag cis-element, as shown in SEQ ID NO: 7, a rev-responsive element (RRE) cis-element, as shown in SEQ ID NO: 8,
an env cis-element, as shown in SEQ ID NO: 9, and
a cPPT cis-element as shown in SEQ ID NO: 10;
the third-generation lentiviral vector comprises:
the lentiviral 5 terminal LTR, as shown in SEQ ID NO: 5,
the lentiviral 3 terminal self-Inactivating LTR, as shown in SEQ ID NO: 6,
the Gag cis-element, as shown in SEQ ID NO: 7,
the RRE cis-element, as shown in SEQ ID NO: 8,
the env cis-element, as shown in SEQ ID NO: 9,
the cPPT cis-element, as shown in SEQ ID NO: 10, and
a Rous-sarcoma-virus (RSV) promoter, as shown in SEQ ID NO: 4.

3. The OCTS-based CAR-T vector of claim 1, wherein, the fifth nucleotide sequence encoding the first PDL1 single-chain antibody light chain, as shown in SEQ ID NO: 16, the sixth nucleotide sequence encoding the second PDL1 single-chain antibody heavy chain, as shown in SEQ ID NO: 17, the seventh nucleotide sequence encoding the first mesothelin single-chain antibody light chain, as shown in SEQ ID NO: 18, the eighth nucleotide sequence encoding the second mesothelin single-chain antibody heavy chain, as shown in SEQ ID NO: 19, the ninth nucleotide sequence encoding the antibody Inner-Linker, as shown in SEQ ID NO: 20, and the tenth nucleotide sequence encoding the single-chain antibody Inter-Linker, as shown in SEQ ID NO: 21, are connected in a sequential way or in a turned way;
wherein, in the sequential way, the fifth nucleotide sequence encoding the first PDL1 single-chain antibody light chain is connected to the seventh nucleotide sequence encoding the first mesothelin single-chain antibody light chain through the tenth nucleotide sequence encoding the single-chain antibody Inter-Linker and is connected to the sixth nucleotide sequence encoding the second PDL1 single-chain antibody heavy chain-through the ninth nucleotide sequence encoding the antibody Inner-Linker, and the seventh nucleotide sequence encoding the first mesothelin single-chain antibody light chain is connected to the eighth nucleotide sequence encoding the second mesothelin single-chain antibody heavy chain through the ninth nucleotide sequence encoding the antibody Inner-Linker; and
in the turned way, the seventh nucleotide sequence encoding the first mesothelin single-chain antibody light chain is connected to the eighth nucleotide sequence encoding the second mesothelin single-chain antibody heavy chain through the ninth nucleotide sequence encoding the antibody Inner-Linker, the fifth nucleotide sequence encoding the first PDL1 single-chain antibody light chain is connected to the eighth nucleotide sequence encoding the second mesothelin single-chain antibody heavy chain through the tenth nucleotide sequence encoding the single-chain antibody Inter-Linker, and the sixth nucleotide sequence encoding the second PDL1 single-chain antibody heavy chain is connected to the seventh nucleotide sequence encoding the first mesothelin single-chain antibody light chain through the antibody Inter-Linker.

4. The OCTS-based CAR-T vector of claim 1, wherein, the PDL1 single-chain antibody is shown in SEQ ID NO: 27.

5. The OCTS-based CAR-T vector of claim 1, wherein, the eWPRE enhanced marmot hepatitis B virus post-transcriptional controlling element has six enhanced nucleotide mutations including: g.396G>A, g.397C>T, g.398T>C, g.399G>A, g.400A>T, and g.411A>T.

6. The OCTS-based CAR-T vector of claim 1, wherein, an expression of the OCTS chimeric receptor structural domain is started by the human EF1αpromoter, and the CD8 leader chimeric receptor signal peptide on a N terminal of OCTS coding sequence is configured to guide a location of OCTS protein on cytomembrane;
a double antigen recognition domain is formed by the PDL1 single-chain antibody light chain, the second PDL1 single-chain antibody heavy chain, the first mesothelin single-chain antibody light chain and the second mesothelin single-chain antibody heavy chain for recognizing target antigens;
the CD8 hinge chimeric receptor linker is configured to anchor scFv on outside of the cytomembrane;
the CD8 transmembrane chimeric receptor transmembrane domain is configured to fix entire chimeric receptors on the cytomembrane;
the CD28 chimeric receptor co-stimulator is configured to stimulate in-vitro T lymphocyte activation and killing effect on in-vivo tumor cells;
the CD134 chimeric receptor co-stimulator is configured to facilitate T lymphocyte proliferation and factor secretion and enhance tumor immunity, contributing to a long-term survival of memory T cells;
the TCR chimeric receptor T cell activation domain is configured to activate an expression of downstream signals; the PDL1 single-chain antibody efficiently binds to PDL1, blocks negative control signals and clinically suppresses tumor immune evasion, thus improving a curative effect of CAR-T in cellular immunotherapy; and
when the double antigen recognition domain is bound to the target antigens, signals are transmitted into cells through chimeric receptors, thereby creating a series of biological effects including T cell proliferation, increased cell factor secretion, increased antiapoptosis secretion, delayed cell death and target cell lysis.

7. The OCTS-based CAR-T vector of claim 1, wherein, the chimeric receptor co-stimulator domain is a combination of CD28 chimeric receptor co-stimulator having a fifteenth nucleotide sequence of SEQ ID NO: 24 and CD134 chimeric receptor co-stimulator having a sixteenth nucleotide sequence of SEQ 1D NO: 25.

8. The OCTS-based CAR-T vector of claim 1, wherein, the first PDL1 single-chain antibody light chain, the second PDL1 single-chain antibody heavy chain, the first mesothelin single-chain antibody light chain, the second mesothelin single-chain antibody heavy chain and the PDL1 single-chain antibody are humanized.

9. A method for preparing the OCTS-based CAR-T vector for targeting the malignant tumors expressing the mesothelin, the PDL1, or both of the mesothelin and the PDL1 according to claim 1, comprising the following steps:
(1) modifying the lentiviral skeleton plasmid to carry the AmpR sequence containing ampicillin resistance gene as shown in SEQ ID NO: 1, the prokaryotic replicon pUC Ori sequence as shown in SEQ ID NO: 2, the virus replicon SV40 Ori sequence as shown in SEQ ID NO: 3, the lentiviral packaging cis-element for lentiviral packaging, the third nucleotide sequence encoding the ZsGreen1 green fluorescent protein as shown in SEQ ID NO: 11, the IRES ribosome binding sequence as shown in SEQ ID NO: 12, and the eWPRE enhanced post-transcriptional regulatory element of Groundhog hepatitis B virus as shown in SEQ ID NO: 13;

(2) combining the human EF1α promoter as shown in SEQ ID NO: 14, the first nucleotide sequence encoding the OCTS chimeric receptor structural domain and the second nucleotide sequence encoding the PDL1 single-chain antibody as shown in SEQ ID NO: 27 into a design scheme for an OCTS chimeric receptor, and cloning the design scheme into the lentiviral skeleton plasmid by digestion, ligation and recombination to obtain recombinant lentiviral plasmids designed by a third-generation OCTS;

(3) transfecting HEK293T/17 cells by the recombinant lentiviral plasmids with lentiviral packaging plasmids pPac-GP and pPac-R and membrane protein pEnv-G respectively; after the recombinant lentiviral plasmids are transcribed and expressed in the HEK293T/17 cells, and recombinant lentiviral vectors packaged successfully are released into cell culture supernatants, collecting supernatants containing the recombinant lentiviral vectors; and (4) purifying the supernatants by column purification of filtration, adsorption and elution to obtain the recombinant lentiviral vectors, respectively.

10. The method of claim 9, wherein, in the step (4), the filtration is performed by controlling a volume of each of the supernatants from 200 ml to 2000 ml with a vacuum degree from −0.5 MPA to 0.9 MPA to prevent a loss of the recombinant lentiviral vectors caused by blockage; the adsorption is performed by controlling a pH value of a solution from 6 to 8 to prevent the recombinant lentiviral vectors from inactivating due to a change of pH, and the elution is performed by controlling an ionic strength of an eluent from 0.5 M to 1.0 M to prevent a change of the ionic strength leading to incomplete elution or inactivation of the recombinant lentiviral vectors.

11. The OCTS-based CAR-T vector of claim 1, wherein, the OCTS-based CAR-T vector is applied in a preparation of drugs for targeting the malignant tumors expressing the mesothelin, the PDL1, or both of the mesothelin and the PDL1.

12. The method of claim 9, wherein, the lentiviral packaging cis-element employs a second-generation lentiviral vector or a third-generation lentiviral vector; wherein
the second-generation lentiviral vector comprises:
a lentiviral 5 terminal long terminal repeat (LTR), as shown in SEQ ID NO: 5,
a lentiviral 3 terminal Self-Inactivating LTR, as shown in SEQ ID NO: 6,
a Gag cis-element, as shown in SEQ ID NO: 7,
a rev-responsive element (RRE) cis-element, as shown in SEQ ID NO: 8,
an env cis-element, as shown in SEQ ID NO: 9, and
a cPPT cis-element as shown in SEQ ID NO: 10;
the third-generation lentiviral vector comprises:
the lentiviral 5 terminal LTR, as shown in SEQ ID NO: 5,
the lentiviral 3 terminal self-Inactivating LTR, as shown in SEQ ID NO: 6,
the Gag cis-element, as shown in SEQ ID NO: 7,
the RRE cis-element, as shown in SEQ ID NO: 8,
the env cis-element, as shown in SEQ ID NO: 9,
the cPPT cis-element, as shown in SEQ ID NO: 10, and
a Rous-sarcoma-virus (RSV) promoter, as shown in SEQ ID NO: 4.

13. The method of claim 9, wherein, the fifth nucleotide sequence encoding the first PDL1 single-chain antibody light chain, as shown in SEQ ID NO: 16, the sixth nucleotide sequence encoding the second PDL1 single-chain antibody heavy chain, as shown in SEQ ID NO: 17, the seventh nucleotide sequence encoding the first mesothelin single-chain antibody light chain, as shown in SEQ ID NO: 18, the eighth nucleotide sequence encoding the second mesothelin single-chain antibody heavy chain, as shown in SEQ ID NO: 19, the ninth nucleotide sequence encoding the antibody Inner-Linker, as shown in SEQ ID NO: 20, and the tenth nucleotide sequence encoding the single-chain antibody Inter-Linker, as shown in SEQ ID NO: 21, are connected in a sequential way or in a turned way;
wherein, in the sequential way, the fifth nucleotide sequence encoding the first PDL1 single-chain antibody light chain is connected to the seventh nucleotide sequence encoding the first mesothelin single-chain antibody light chain through the tenth nucleotide sequence encoding the single-chain antibody Inter-Linker and is connected to the sixth nucleotide sequence encoding the second PDL1 single-chain antibody heavy chain through the ninth nucleotide sequence encoding the antibody Inner-Linker, and the seventh nucleotide sequence encoding the first mesothelin single-chain antibody light chain is connected to the eighth nucleotide sequence encoding the second mesothelin single-chain antibody heavy chain through the ninth nucleotide sequence encoding the antibody Inner-Linker; and
in the turned way, the seventh nucleotide sequence encoding the first mesothelin single-chain antibody light chain is connected to the eighth nucleotide sequence encoding the second mesothelin single-chain antibody heavy chain through the ninth nucleotide sequence encoding the antibody Inner-Linker, the fifth nucleotide sequence encoding the first PDL1 single-chain antibody light chain is connected to the eighth nucleotide sequence encoding the second mesothelin single-chain antibody heavy chain through the tenth nucleotide sequence encoding the single-chain antibody Inter-Linker, and the sixth nucleotide sequence encoding the second PDL1 single-chain antibody heavy chain is connected to the seventh nucleotide sequence encoding the first mesothelin single-chain antibody light chain through the antibody Inter-Linker.

14. The method of claim 9, wherein, the PDL1 single-chain antibody is shown in SEQ ID NO: 27.

15. The method of claim 9, wherein, the eWPRE enhanced marmot hepatitis B virus post-transcriptional controlling element has six enhanced nucleotide mutations including: g.396G>A, g.397C>T, g.398T>C, g.399G>A, g.400A>T, and g.411A>T.

16. The method of claim 9, wherein,
an expression of the OCTS chimeric receptor structural domain is started by the human EF1α promoter, and the CD8 leader chimeric receptor signal peptide on a N terminal of OCTS coding sequence is configured to guide a location of OCTS protein on cytomembrane;
a double antigen recognition domain is formed by the PDL1 single-chain antibody light chain, the second PDL1 single-chain antibody heavy chain, the first mesothelin single-chain antibody light chain and the second mesothelin single-chain antibody heavy chain for recognizing target antigens;
the CD8 hinge chimeric receptor linker is configured to anchor scFv on outside of the cytomembrane;
the CD8 transmembrane chimeric receptor transmembrane domain is configured to fix entire chimeric receptors on the cytomembrane;

the CD28 chimeric receptor co-stimulator is configured to stimulate in-vitro T lymphocyte activation and killing effect on in-vivo tumor cells;

the CD134 chimeric receptor co-stimulator is configured to facilitate T lymphocyte proliferation and factor secretion and enhance tumor immunity, contributing to a long-term survival of memory T cells;

the TCR chimeric receptor T cell activation domain is configured to activate an expression of downstream signals; the PDL1 single-chain antibody efficiently binds to PDL1, blocks negative control signals and clinically suppresses tumor immune evasion, thus improving a curative effect of CAR-T in cellular immunotherapy; and when the double antigen recognition domain is bound to the target antigens, signals are transmitted into cells through chimeric receptors, thereby creating a series of biological effects including T cell proliferation, increased cell factor secretion, increased antiapoptosis secretion, delayed cell death and target cell lysis.

17. The method of claim 9, wherein, the chimeric receptor co-stimulator domain is a combination of CD28 chimeric receptor co-stimulator having a fifteenth nucleotide sequence of SEQ ID NO: 24 and CD134 chimeric receptor co-stimulator having a sixteenth nucleotide sequence of SEQ ID NO: 25.

18. The method of claim 9, wherein, the first PDL1 single-chain antibody light chain, the second PDL1 single-chain antibody heavy chain, the first mesothelin single-chain antibody light chain, the second mesothelin single-chain antibody heavy chain and the PDL1 single-chain antibody are humanized.

19. The OCTS-based CAR-T vector of claim 2, wherein, the OCTS-based CAR-T vector is applied in a preparation of drugs for targeting the malignant tumors expressing the mesothelin, the PDL1, or both of the mesothelin and the PDL1.

20. The OCTS-based CAR-T vector of claim 3, wherein, the OCTS-based CAR-T vector is applied in a preparation of drugs for targeting the malignant tumors expressing the mesothelin, the PDL1, or both of the mesothelin and the PDL1.

* * * * *